(12) United States Patent
Gutkowicz-Krusin et al.

(10) Patent No.: US 6,208,749 B1
(45) Date of Patent: *Mar. 27, 2001

(54) SYSTEMS AND METHODS FOR THE MULTISPECTRAL IMAGING AND CHARACTERIZATION OF SKIN TISSUE

(75) Inventors: Dina Gutkowicz-Krusin, Princeton, NJ (US); Marek Elbaum, Dobbs Ferry; Michael Greenebaum, Brooklyn, both of NY (US); Adam Jacobs, Glen Ridge, NJ (US)

(73) Assignee: Electro-Optical Sciences, Inc., Irvington, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,450

(22) Filed: Feb. 27, 1998

Related U.S. Application Data

(60) Provisional application No. 60/039,218, filed on Feb. 28, 1997, and provisional application No. 60/039,407, filed on Feb. 28, 1997.

(51) Int. Cl.[7] ............................. G06K 9/00; G06K 9/34; G01J 3/40
(52) U.S. Cl. ......................... 382/128; 382/165; 382/173; 356/303
(58) Field of Search ................................. 382/128, 162, 382/173, 274, 165; 358/504; 356/303, 346

(56) References Cited

U.S. PATENT DOCUMENTS

| | | |
|---|---|---|
| 3,335,716 | 8/1967 | Alt et al. |
| 4,170,987 | 10/1979 | Anselmo et al. ................. 600/475 |
| 4,236,082 | 11/1980 | Butler ............................... 250/461.1 |
| 4,505,583 | 3/1985 | Konomi ............................... 356/73 |
| 4,556,057 | 12/1985 | Hiruma et al. ....................... 600/476 |

(List continued on next page.)

FOREIGN PATENT DOCUMENTS

| | | | |
|---|---|---|---|
| 0359433 | 3/1990 | (EP) | ................................. A61B/5/05 |
| 0650694 | 5/1995 | (EP) | ................................. A61B/5/00 |

OTHER PUBLICATIONS

S.X. Zhao and T. Lu, "The Classification of the Depth of Burn Injury Using Hybrid Neural Network"; IEEE Conference on Engineering in Medicine & Biology Society, ISBN 7803–2475–7, vol. 1, pp. 815–816, Jul., 1997.

I. Koren, A. Laine, F. Taylor, M. Lewis, "Interactive Wavelet Processing and Techniques Applied to Digital Mammography"; IEEE Conference Proceedings, ISBN 07–7803–3 192–3, vol. 3, pp. 1415–1418, Mar. 1996.

(List continued on next page.)

*Primary Examiner*—Amelia Au
*Assistant Examiner*—Mehrdad Dastouri
(74) *Attorney, Agent, or Firm*—Morgan & Finnegan, L.L.P.

(57) ABSTRACT

Systems and methods for the multispectral imaging of skin tissue enables automatic characterization of the condition of a region of interest of the skin, based on direct digital imaging of the region of interest or the digitization of color photographic slides of the region of interest, illuminated by appropriately filtered light. Preferably, a digital image at a low spectral band is automatically segmented and that segmented mask is used to segment the other images by a digital processor. Parameters related to the texture, asymmetry, blotchiness and border irregularities are also automatically estimated. The region of interest is automatically characterized by the digital processor, based on those parameters. The region of interest may include a skin lesion, in which case the present invention enables the characterization of the lesion as malignant or benign.

73 Claims, 16 Drawing Sheets

U.S. PATENT DOCUMENTS

| | | | |
|---|---|---|---|
| 4,768,513 | 9/1988 | Suzuki | 600/476 |
| 4,773,097 | 9/1988 | Suzaki et al. | 382/128 |
| 4,821,117 | 4/1989 | Sekiguchi | 348/68 |
| 4,894,547 | 1/1990 | Leffell et al. | 250/461.2 |
| 4,930,516 | 6/1990 | Alfano et al. | 600/477 |
| 4,957,114 | 9/1990 | Zeng et al. | 600/476 |
| 5,003,977 | 4/1991 | Suzuki et al. | 600/317 |
| 5,016,173 | 5/1991 | Kenet et al. | 382/128 |
| 5,036,853 | 8/1991 | Jeffcoat et al. | 600/342 |
| 5,157,461 | 10/1992 | Page | 356/350 |
| 5,174,297 | 12/1992 | Daikuzono | 600/476 |
| 5,241,468 | 8/1993 | Kenet | 600/300 |
| 5,363,854 | 11/1994 | Martens et al. | 600/477 |
| 5,369,496 | 11/1994 | Alfano et al. | 600/477 |
| 5,408,996 | 4/1995 | Salb | 600/317 |
| 5,421,337 | 6/1995 | Richards-Kortum et al. | 600/477 |
| 5,515,449 | 5/1996 | Tsuruoka et al. | 382/128 |
| 5,528,703 | 6/1996 | Lee | 382/257 |
| 5,590,660 | 1/1997 | MacAulay et al. | 600/478 |
| 5,660,982 * | 8/1997 | Tryggvason et al. | 435/6 |
| 5,699,798 | 12/1997 | Hochman et al. | 600/420 |
| 5,701,902 | 12/1997 | Vari et al. | 600/473 |
| 5,717,791 | 2/1998 | Labaere et al. | 382/274 |
| 5,740,268 | 4/1998 | Nishikawa et al. | 382/132 |
| 5,749,830 | 5/1998 | Kaneko et al. | 600/160 |
| 5,784,162 | 7/1998 | Cabib et al. | 356/346 |
| 5,799,100 | 8/1998 | Clarke et al. | 382/132 |

OTHER PUBLICATIONS

T. Lee, V. Ng, D. McLean, A. Coldman, R. Gallagher and J. Sale, "A Multi-Stage Segmentation Method for Images of Skin Lesions"; IEEE Conference Proceedings on Communication, Computers and Signal Processing, pp. 602–605, Feb. 1995.

B.F. Jones and P. Plassman, "An Instrument to Measure the Dimensions of Skin Wounds"; IEEE Transactions on Biomedical Engineering, vol. 42, No. 5, pp. 464–470, May 1995.

R.T.J. Bostock, E. Claridge, A.J. Harget, and P.N. Hall, "Towards A Neural Network Based System For Skin Cancer Diagnosis"; IEEE International Conference on Artificial Neural Networks, pp. 215–219, ISBN 0–85296–573–7, 1993.

M. Herbin, A. Venot, J.Y. Devaux and C. Piette, "Color Quantitation Through Image Processing in Dermatology"; IEEE Transactions on Medical Imaging, vol. 9, No. 1, pp. 262–269, Sep. 1990.

"Border irregularity: atypical moles versus melanoma", C.L. Huang et al., Eur J Dermatol, vol. 6, pp. 270–273, Jun. 1996.

"In vivo Spectrophotometric Evaluation of Neoplastic and Non–Neoplastic Skin Pigmented Lesions. III. CCD Camera–Based Reflectance Imaging", R. Marchesini et al., Photochemistry and Photobiology, vol. 62, No. 1, pp. 151–154; 1995.

"The Morphologic Criteria of the Pseudopod in Surface Microscopy", S.W. Menzies, et al., Arch Dermatol, vol. 131, pp. 436–440, Apr. 1995.

"A rudimentary system for automatic discrimination among basic skin lesions on the basis of color analysis of video images", H. Takiwaki et al., Journal of the American Academy of Dermatology, vol. 32, No. 4, pp. 600–604, Apr. 1995.

"Topodermatographic Image Analysis for Melanoma Screening and the Quantitative Assessment of Tumor Dimension Parameters of the Skin", H. Voigt et al., Cancer, vol. 75, No. 4, Feb. 15, 1995.

"Application of an artificial neural network in epiluminescence microscopy pattern analysis of pigmented skin lesions: a pilot study", M. Binder et al., British Journal of Dermatology 130; pp. 460–465; 1994.

"Computer image analysis in the diagnosis of melanoma", A. Greene et al., Journal of the American Academy of Dermatology; vol. 31, No. 6, pp. 958–964, 1994.

"Computerized Digital Image Analysis: An Aid for Melanoma Diagnosis", A.J. Sober et al., The Journal of Dermatology, vol. 21, pp. 885–890, 1994.

"Neural Network Diagnosis of Malignant Melanoma From Color Images", F. Ercal et al., IEEE Transactions of Biomedical Engineering, vol. 41, No. 9, pp. 837–845, Sep. 1994.

"The ABCD rule of dermatology", F. Nachbar et al., Journal of the American Academy of Dermatology, vol. 3, No. 4, pp. 551–559, Apr. 1994.

"Evaluation of different image acquisition techniques for a computer vision system in the diagnosis of malignant melanoma", T. Schindewolf et al., Journal of the American Academy of Dermatology, vol. 31, No. 1, pp. 33–41, Jul. 1994.

"Detection of Skin Tumor Boundaries in Color Images", F. Ercal et al., IEEE Transactions of Medical Imaging, vol. 12, No. 3, pp. 624–627, Sep. 1993.

"Automatic Color Segmentation Algorithms with Application to Skin Tumor Feature Identification", S.E. Umbagh et al., IEEE Engineering in Medicine and Biology, pp. 75–82, Sep., 1993.

"Comparison of classification rates for conventional and dermatoscopic images of malignant and benign melanocytic lesions using computerized colour image analysis", T. Schindewolf et al., Eur J Dermatol, vol. 3, No. 4, pp. 299–303, May 1993.

"Classification of Melanocytic Lesions with Color and Texture Analysis Using Digital Image Processing", T. Schindewolf et al., The International Academy of Cytology, Analytical and Quantitative Cytology and Histology, vol. 15, No. 1, pp. 1–11, Feb. 1993.

"Clinical Diagnosis of Pigmented Lesions Using Digital Epiluminescence Microscopy", R.O. Kenet et al., Arch Dermatol, vol. 129, pp. 157–174; Feb. 1993.

"Optical properties of human dermis in vitro and in vivo", R. Graaff et al., Applied Optics, vol. 32, No. 4, pp. 435–447, Feb. 1, 1993.

"Automatic Detection of Irregular Borders in Melanoma and Other Skin Tumors", J.E. Golston et al., Computerized Medical Imaging and Graphics, vol. 16, No. 3, pp. 199–203, 1992.

"Automatic Detection of Asymmetry in Skin Tumors", W.V. Stoecker et al., Computerized Medical Imaging and Graphics, vol. 16, No. 3, pp. 191–197, 1992.

"Results obtained by using a computerized image analysis system designed as an aid to diagnosis of cutaneous melanoma", N. Cascinelli et al., Melanoma Research, vol. 2, pp. 163–170, 1992.

"An Automatic Color Segmentation Algorithm with Application to Identification of Skin Tumor Borders", S.E. Umbaugh et al., Computerized Medical Imaging and Graphics, vol. 16, No. 3, pp. 227–235, May–Jun. 1992.

"Automatic Color Segmentation of Images with Application to Detection of Variegated Coloring in Skin Tumors", S.W. Umbaugh et al., IEEE Engineering in Medicine and Biology Magazine, Dec. 1989, pp. 43–52.

"Multispectral Imaging of Burn Wounds: A New Clinical Instrument for Evaluating Burn Depth", M.A. Afromowitz et al., IEEE Transactions on Biomedical Engineering, vol. 35, No. 10, pp. 842–850; Oct. 1988.

"In vivo epiluminescence microscopy of pigmented skin lesions. I. Pattern analysis of pigmented skin lesions", H. Pehamberger et al., Journal of American Academy of Dermatology, vol. 17, No. 4, pp. 571–583, Oct. 1987.

"In vivo epiluminescence microscopy of pigmented skin lesions. II. Diagnosis of small pigmented skin lesions and early detection of malignant melanoma", A. Steiner et al., Journal of the American Academy of Dermatology, vol. 17, No. 4, pp. 584–591; Oct. 1987.

"The Optics of Human Skin", R.R. Anderson et al., The Journal of Investigative Dermatology, vol. 77, No. 1, pp. 13–19; Jul. 1981.

"Melanin, a unique biological absorber", M.L. Wolbarsht, Applied Optics, vol. 20, No. 13, pp. 2184–2186; Jul. 1, 1981.

"The Wavelet Transform, Time–Frequency Localization and Signal Analysis", I. Daubechies, IEEE Trans Inform Theory, vol. 36, No. 5, pp. 961–1005; Sep. 1990.

"Wavelet in Medicine and Biology", Aldroubi et al., C&C Press, NY, pp. 11–15, 1996.

"Singularity detection and processing with wavelets", S. Mallat et al., IEEE Trans Inform Theory 38:617–643; 1992.

"Wavelets and Applications", S. Mallat et al., S. Verlag; Y. Meyer (ed.) NY pp. 207–284; 1992.

"Characterization of signals from multiscale edges", S. Mallat et al., IEEE Trans Patt and Mech Int'l; 14:710–732; 1992.

"Introduction to Statistical Pattern Recognition", K. Fukumaga, Academic Press, Boston, pp. 90–96, 125, 219–221; 1990.

"Image Features From Phase Congruency", P. Kovesi, University of Western Australia, pp. 1–30; Technical Report 9/4, Revised Jun. 1995.

* cited by examiner

MALIGNANT MELANOMA          ATYPICAL MELANOCYTIC NEVUS

MALIGNANT MELANOMA          ATYPICAL MELANOCYTIC NEVUS

MALIGNANT MELANOMA　　　ATYPICAL MELANOCYTIC NEVUS

|   | I−3 | I−2 | I−1 | I | I+1 | I+2 | I+3 |
|---|---|---|---|---|---|---|---|
| J−5 | 0 | 1 | 0 | 0 | 0 | 1 | 0 |
| J−4 | 0 | 1 | 1 | 0 | 1 | 1 | 0 |
| J−3 | 0 | 0 | 2 | 3 | 2 | 0 | 0 |
| J−2 | 1 | 0 | 0 | 1 | 0 | 0 | 1 |
| J−1 | 1 | 0 | −3 | −5 | −3 | 0 | 1 |
| J | 1 | 1 | −5 | −8 | −5 | 1 | 1 |
| J+1 | 1 | 0 | −3 | −5 | −3 | 0 | 1 |
| J+2 | 1 | 0 | 0 | 1 | 0 | 0 | 1 |
| J+3 | 0 | 0 | 2 | 3 | 2 | 0 | 0 |
| J+4 | 0 | 1 | 1 | 0 | 1 | 1 | 0 |
| J+5 | 0 | 1 | 0 | 0 | 0 | 1 | 0 |

Fig. 9

MALIGNANT MELANOMA        ATYPICAL MELANOCYTIC NEVUS

| PARAMETER | | Diagnostic accuracy (%) | Sensitivity (%) | Specificity (%) |
|---|---|---|---|---|
| Asymmetry: | $A_{bin}$ | 52 | 71 | 86 |
| | $A_b$ | 48 | 68 | 84 |
| | $A_g$ | 50 | 73 | 82 |
| | $A_r$ | 62 | 78 | 89 |
| Blotchiness: | $Bl_b$ | 45 | 56 | 90 |
| | $Bl_g$ | 40 | 68 | 72 |
| | $Bl_r$ | 42 | 68 | 75 |
| | $C_b$ | 37 | 80 | 55 |
| | $C_r$ | 38 | 80 | 57 |
| | $Cl$ | 44 | 78 | 70 |
| Border: | $B$ | 44 | 66 | 81 |
| | $G_b$ | 36 | 76 | 56 |
| Texture: | $T1_b$ | 38 | 88 | 49 |
| | $T1_g$ | 49 | 61 | 90 |
| | $T2_g$ | 41 | 66 | 76 |
| | $T2_r$ | 43 | 73 | 72 |
| | $T3_b$ | 39 | 80 | 59 |
| | $T3_g$ | 38 | 63 | 74 |
| | $T4_b$ | 38 | 68 | 69 |
| | $T4_g$ | 39 | 56 | 83 |
| | $T5_b$ | 36 | 76 | 58 |
| | $T6_b$ | 38 | 90 | 46 |

Fig. 11

SYSTEMS AND METHODS FOR THE MULTISPECTRAL IMAGING AND CHARACTERIZATION OF SKIN TISSUE

This application claims the benefit of U.S. provisional application Ser. Nos. 60/039,218 and 60/039,407, both of which were filed on Feb. 28, 1997, and are incorporated by reference, herein.

STATEMENT REGARDING FEDERALLY SPONSORED RESEARCH

This invention was made with Government support under NIH/National Cancer Institute Contract No. 2-R44-CA60229-02A1 and U.S.A.F. Phillips Laboratory Contract No. F29601-95-C-0125. The Government has certain rights in this invention.

FIELD OF THE INVENTION

This invention relates to methods and systems for the computer controlled image analysis of digital skin tissue at a plurality of wavelengths, which may include those outside of the red-green-blue bands. The methods and systems further include the automatic characterization of the condition of the skin tissue, based on automatically computed values of parameters which are functions of characteristics of the skin tissue, based on the digital images. Skin lesions can be analyzed for determining whether the lesion is a melanoma, for example. Systems for digitally imaging and analyzing skin tissue are disclosed, as well.

BACKGROUND OF THE INVENTION

Melanoma is a usually fatal skin cancer, unless it is detected and surgically removed in its earliest stages. Early detection of malignant melanoma is difficult because early melanomas, those having a Breslow thickness less than 1 mm, share many diagnostic features with benign lesions, such as dysplastic nevi or atypical melanocytic nevi.

To aid in the analysis of lesions, conventional photography, referred to as "clinical imaging", has been used to image the lesion for further study. The effectiveness of clinical imaging can be compromised, however, by specular reflection by the skin. Polarizers have been used for polarized imaging, which minimizes specular reflection.

Dermoscopy is another technique for examining skin, in which specular reflection is minimized. Dermoscopy also assists in clinically differentiating melanoma from its benign simulants by enabling the observation of features of pigmented melanocytic lesions that are not discernible by the naked eye. In dermoscopy, the skin is made more transparent to light by providing an oil layer over the skin, in front of the optical system. A glass plate is placed over the oil layer. The oil has an index of refraction between the index of refraction of the horny layer of the skin and the glass plate. Standard magnifying optics may be used to enlarge the structures rendered visible on and under the surface of the skin by the oil layer. The region of interest can then be examined visually. Slides of the region of interest can be made, as well, for future study.

Despite their similarities, most malignant melanomas differ in certain of their characteristics from other melanocytic lesions. A major advance in characterizing skin lesions based on certain of the observable differences between malignant and other lesions is the "ABCD" rule, where A=asymmetry, B=border irregularity, C=color variability, and D=diameter greater than 6 mm. A corresponding ABCD rule, where "D" refers to dermoscopic structures, such as brown globules, black dots or pigment networks within the lesion, is applied to dermoscopic images. Because the clinical and dermoscopic applications of these rules are subjective, they are not very reliable.

When skin is illuminated by light, the light can be re-emitted by reflection, scattering or fluorescence. It is known in the art that the re-emission of light absorbed at different wavelengths by a region of interest of skin can provide different information. For example, as the wavelength of the light increases, its depth of penetration into the skin or other tissue also increases. Chromophores at different depths in the tissue therefore absorb and re-emit light at various wavelengths. Melanin and hemoglobin are examples of such chromophores.

Since the unaided eye cannot perceive light outside of the visible region or low-contrast structure in visible-light images, information which may be useful in diagnosing a lesion may not be directly observable. Digital acquisition and processing of dermoscopic images may, therefore, improve diagnostic reliability by employing more of the information residing in such images that is not directly observable. There have therefore been attempts to use objective, computer-based, image analysis algorithms that can discern meaningful differences between benign and malignant melanocytic lesions with sufficient accuracy.

Computer processing of images requires that the image be in digital form. A digital image is an array of digital signals whose values are a function of certain characteristics of the subject of the image. When imaging skin lesions, the digital images comprise digital signals whose values are a function of the re-emission characteristics of the skin and lesion, at different spectral bands of light. The array is obtained by spatial sampling and quantizing the intensity of images obtained with film or directly by electronic cameras. Practical limitations on the number of picture elements or pixels per unit area of image determine the achievable spatial resolution of the digital image. The digital image typically needs to be segmented to separate the digital signals which are a function of the skin lesion from the digital signals which are a function of the surrounding skin.

Computer aided analysis has also been used to classify skin lesions using quantitative values indicative of particular characteristics of lesions, referred to as parameters. Based on histopathological diagnosis of lesions, algorithms have been developed which use linear or non-linear classifiers to combine parameters provided by the operator of an imaging device or a physician or computed by a processor, to yield a value which can be used to classify the lesion. Because some of the steps in the computer-aided analysis of which we are aware depend on subjective judgments of an individual, such analyses may provide highly variable results.

The images heretofore available have been obtained with commercially available red-green-blue color imaging apparatus. Color photographic transparencies of skin lesions have been digitized and skin lesions have been directly imaged with "three-chip" digitizing cameras. Such cameras employ broad-band filter bandpasses that are ultimately based on the wavelength response of the human visual system and have large regions of overlap.

Electronic images may also be obtained in narrower, non-overlapping filter bandpasses, which may reveal additional, wavelength-dependent differences between the images of melanomas and of benign lesions. However, such devices have had poor resolution and/or poor signal-to-noise characteristics which prevent the acquisition of digital images of melanocytic skin lesions of sufficient quality for effective application of machine vision techniques for lesion diagnosis.

Existing imaging systems and processes also tend to suffer from an inability to provide the required repeatability of the values of extracted lesion parameters, due in part to a lack of standardization with respect to spatially varying artifacts. The parameters, therefore, lack invariance to lighting and image exposure conditions, for example. Obtaining high signal-to-noise ratios in images recorded in narrow filter bandpasses, when exposure times are sufficiently short that the skin is effectively "frozen" during the exposure sequence, has also been difficult. In addition, since the optimum wavelengths for automatic characterization may not be the optimum wavelengths for visual observation, it may be difficult to reconstruct high-fidelity color images from the digital images for visual interpretation by a clinician.

The assessment of wounds and burns through the appearance of color images present similar challenges. Existing technology for the imaging of skin in vivo for these purposes is also inadequate. Practical solutions to the problems of employing multispectral digital imaging of skin for the analysis of lesions, wounds, or other conditions have not been found.

SUMMARY OF THE INVENTION

The methods and systems of the present invention provide for the acquisition of digital images of skin at a plurality of spectral bands to automatically characterize the condition of the tissue based on the digital images. Spectral wavelength bands within and outside of the visible band may be used. In accordance with the present invention, a pigmented skin lesion can be characterized as malignant or benign, for example. The digital images comprise a plurality of digital signals whose values are functions of the condition of the tissue. The digital images acquired are subjected to objective and quantitative analysis by a digital processor to detect and identify abnormalities. The analysis includes image segmentation, parameter estimation and characterization of the skin. The estimation and characterization steps are automatic. The segmentation step may be automatic, as well. Subjective judgments are therefore minimized or eliminated.

It has been found that generating the segmentation mask from a digital image acquired with light in a spectral band which does not penetrate deeply into the skin, such as a blue spectral band, provides superior results. After segmentation, estimated values which are functions of characteristics of the lesion, such as its texture, asymmetry, blotchiness, and border irregularities, are computed and used to automatically characterize the condition of the skin. Digital signals corresponding to hair or blob-like structures are preferably removed during segmentation.

In accordance with the present invention, a method for characterizing the condition of a region of interest of the skin, wherein the absorption and scattering of light in different spectral bands by the region of interest is a function of the condition of the skin, is disclosed. The method comprises illuminating the region of interest of the skin by light in at least three spectral bands and digitally imaging the region of interest at the at least three spectral bands with the light re-emitted by the skin to generate digital images comprising digital signals whose values are a function of the condition of the skin. The digital images are provided to a processor which segments the digital images by generating a segmentation mask from a digital image in any one of the at least three spectral bands, computes at least one estimated value for each digital image at each spectral band which is a function of a characteristic of the region of interest within the segmentation mask, characterizes the condition of the skin based on the estimated values, and outputs the characterization of the condition of the skin. Preferably, the segmenting, estimating and characterizing steps are conducted without the intervention of an operator. Useful parameters include measures of the texture, asymmetry, blotchiness and border irregularity of the portion of the region of interest.

The digital images may be obtained by directly imaging the region of interest with a digital camera, or digitally imaging color slides of the region of interest, through appropriately filtered light.

The characterizing step may include comparing a weighted combination of the parameter values against a threshold value. The weight coefficients for each parameter value and the threshold value may be selected based on a training set of images of lesions or other skin conditions, whose condition has been determined, preferably through histological examination by a plurality of doctors. Preferably, specificity is maximized under the constraint of 100% sensitivity to melanoma.

In accordance with another aspect of the invention, a system for characterizing the condition of a region of interest of skin includes means for illuminating the region of interest with light in at least three spectral bands and a camera for acquiring digital images of the region of interest based on the light re-emitted from the illuminated region of interest at each of the spectral bands. The digital image comprises digital signals whose values are a function of the condition of the region of interest. A digital processor segments the digital images by generating a segmentation mask from a digital image in any one of the at least three spectral bands, and computes at least one estimated value for each digital image at each spectral band which is a function of the texture of the portion of the region of interest within the segmentation mask. The processor characterizes the lesion based on the estimated value or values. The other parameters discussed above may be used, as well.

The camera may be a single-chip or multiple-chip charge-coupled device which detects light in a plurality of spectral bands between the near ultraviolet to near infrared. The filter means may be a plurality of interference filters mounted on a wheel for stepping any filter into a position intercepting the light from the light source. Preferably, at least one of the spectral bands has a center which lies between about 400 and 500 nanometers, at least one of the spectral bands has a center which lies between about 500 and 600 nanometers, and at least one other spectral band has a center which lies between about 750 and 1000 nanometers.

DESCRIPTION OF THE FIGURES

FIG. 9 is a spatial filter used to remove hair;

FIG. 11 is a chart of lesion parameters and their associated diagnostic accuracy, sensitivity and specificity when used individually;

DESCRIPTION OF THE INVENTION

Figure 1A:
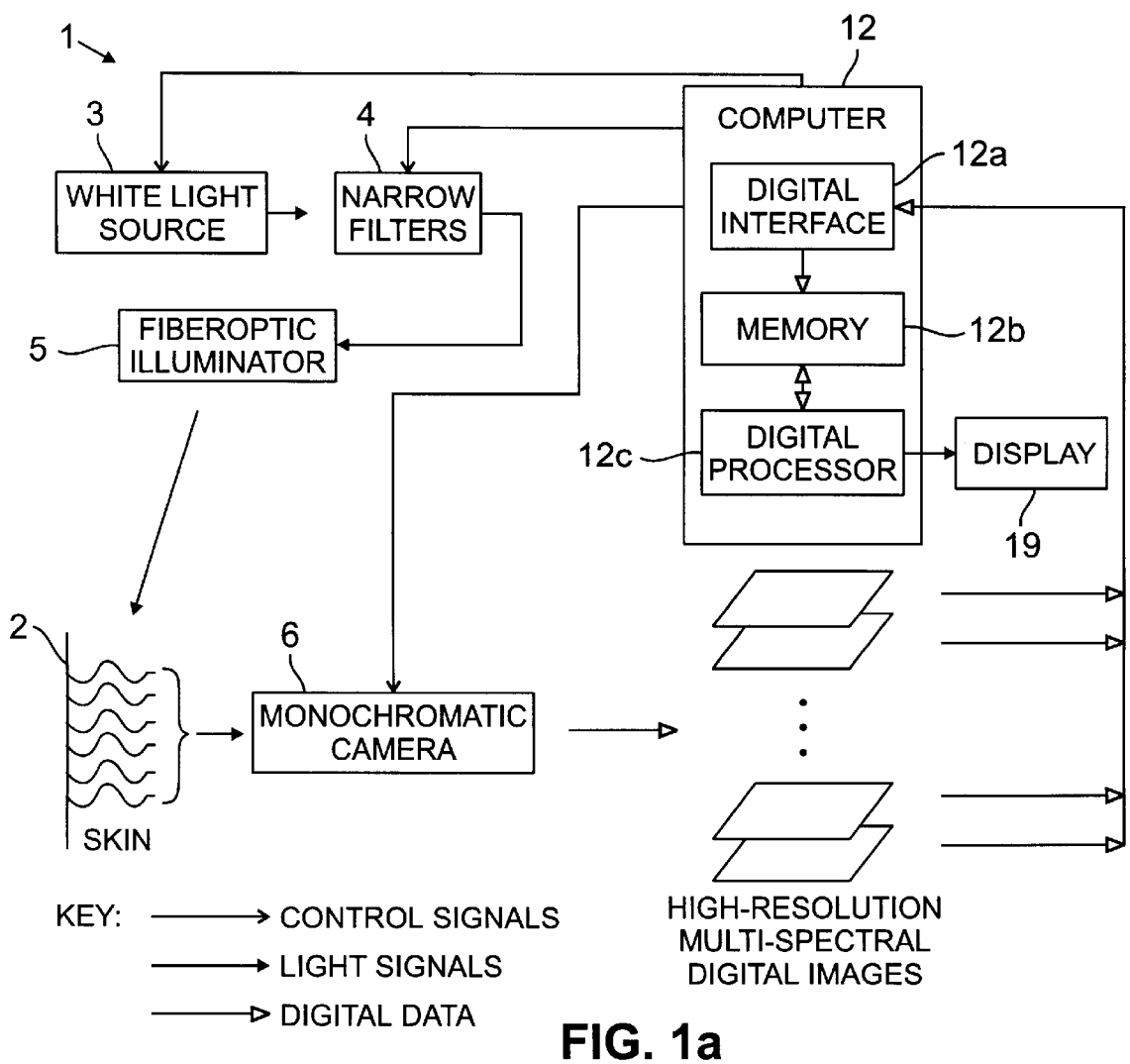
FIG. 1(a) is a schematic illustration of a method and system of imaging a region of interest of skin in accordance with the present invention.

FIG. 1(a) is a schematic illustration of a method and system 1 in accordance with the present invention, by which images of the skin 2 are acquired by a camera nearly simultaneously at a plurality of spectral bands, $\lambda_i$, i=1,2,... M, that are preferably effectively non-overlapping, as shown schematically in FIG. 1(b). The skin is illuminated by a source of white light 3, which is filtered by narrow passband filters 4. The filtered light is preferably conveyed to the skin 2 through a fiberoptic illuminator 5. The light re-emitted by the illuminated skin is imaged by a low-noise, high-resolution monochrome camera 6, which is preferably an electronic charge-coupled ("CCD") camera. Digital images output by the camera 6 are provided to a computer 12 for processing.

The computer 12 includes a digital interface 12a, a memory 12b and a digital processor 12c. A display 19 is preferably provided as well. The computer 12 includes an input to a digital interface 12a for receiving the digital images. A memory 12b stores the digital images, and the software controlling operation of the imaging system, the image processing, and the classification and characterization of the lesion. The digital processor 12c, under control of the software, performs the calculations. The computer 12 has an output connected to a display 19, which can display the processed images and the results of the classification and characterization procedures for each image. The computer 12 also preferably has outputs connected to the source of light 3 and the camera 6, for controlling their illumination level and exposure times, respectively, as described below.

The image processing, classification or characterization and other programs can be implemented on a personal computer, using a programming language, such as FORTRAN or C. The memory 12b which stores the software can be any convenient media readable by the computer 12, such as the hard drive of the computer, read only memory, random access memory with a battery backup, electrically programmed ROM, electrically erasable ROM, floppy disc, or CD ROM. Other suitable media may be used, as well.

Figure 1B:
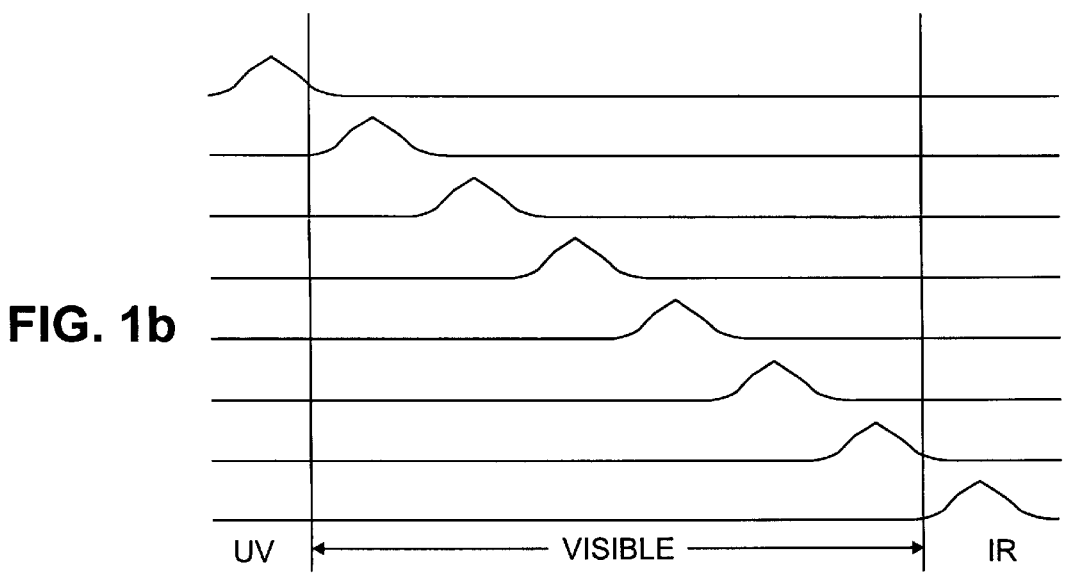
FIG. 1(b) is a schematic illustration of a plurality of narrow spectral bandwidths which may be used to illuminate the skin in the embodiment of FIG. 1(a)

When the filter bandpasses have minimal overlap, as in FIG. 1(b), each monochromatic image will contain spectrally independent information. Such spectral separation is believed to be useful for differential diagnosis of skin lesions that contain varying amounts of melanin, and of hemoglobin in different oxidation states, for example. Spectral separation is also believed to be useful in distinguishing granulation of tissue and other structural details of wounds in various stages of healing. One or more of the wavelength bands may lie outside the visible region, such as in the near infrared and/or the near ultraviolet, as long as the wavelength is within the response range of the combined optical system including the electronic camera 6.

Figure 1C:
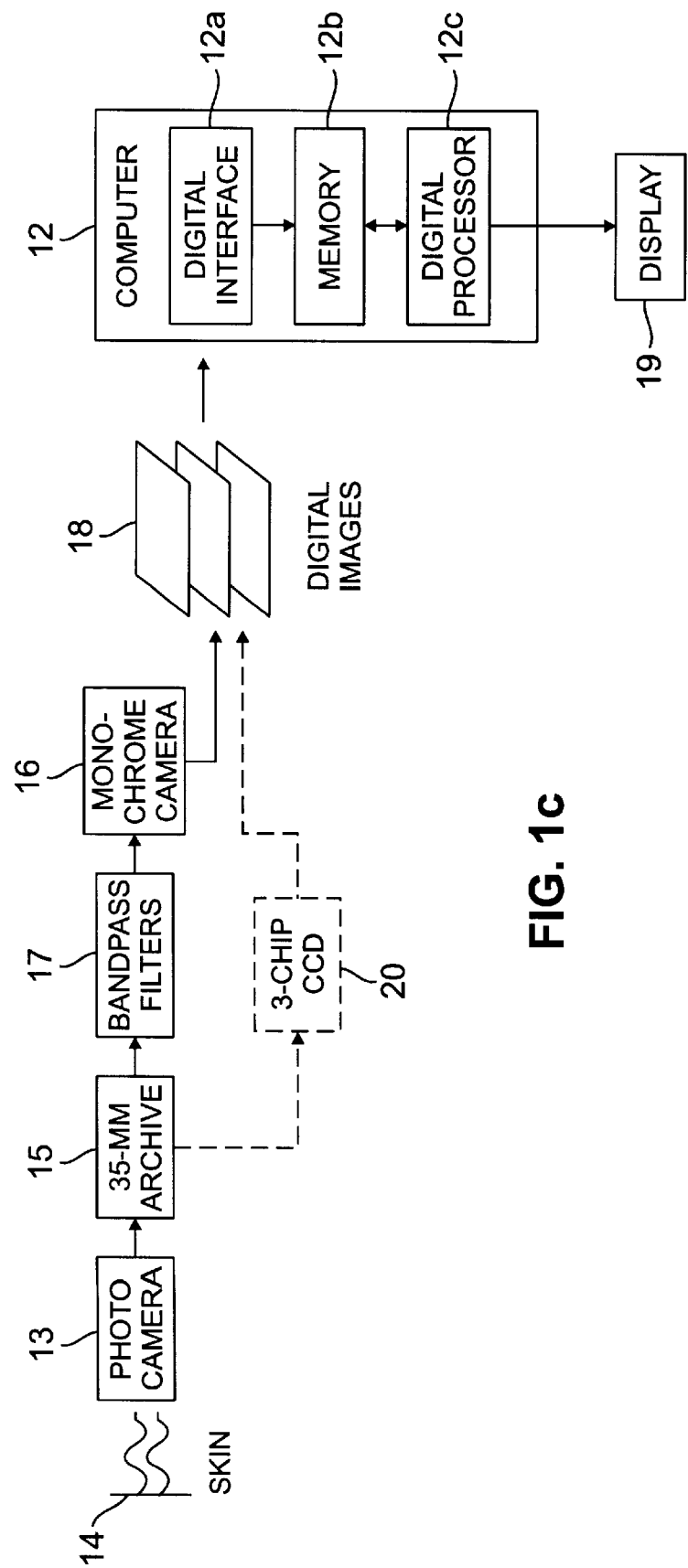
FIG. 1(c) is a schematic illustration of alternative methods and systems for digitizing and analyzing color photographic slides of a region of interest of skin.

In accordance with another aspect of the invention, the digital images of skin lesions can be derived from color slides of the lesions obtained by clinical imaging, dermoscopy, or polarization imaging. FIG. 1(c) is a schematic illustration of alternative approaches to the acquisition and digitization of images of skin lesions from color slides. A photo camera 13 produces 35-mm color slides of a region of the skin 14. The camera 13 can be a Dermaphot® camera from Heine, Optotechnik Gmbh & Co. AG, Germany, for example. The slides are typically stored in an archive 15. The slides are subsequently reimaged by a monochrome camera 16, which may be a CCD camera, that photographs each slide as it is illuminated by white light that has passed through a sequence of bandpass filters 17 to create a color filtered version of the image. The slides can be illuminated at broad or narrow blue (B), green (G) and red (R) wavelength bands, respectively. The broad wavelength bands may overlap somewhat. In one example, the blue wavelength band was about 400 nm±30 nm, the green wavelength band was about 550 nm±30 nm, and the red wavelength band was about 700 nm±30 nm.

Each of the filtered representations is recorded by the monochrome camera 16, which provides the resulting digital images 18 to an input of the computer 12. If a CCD camera is not used, the slide images could be digitized by any available commercial digitizer including three channels, one for red, one for green and one for blue, as long as the pixel size in the lesion plane after digitization is less than about 60 micrometers ("$\mu$m").

An appropriate CCD camera 16 is available from Electrim, Inc., Princeton, N.J. The camera 16 has a photographic macro-lens, wherein f#/2.8 and f=100 mm. Preferably, the spatial resolution of the CCD camera 16 provides pixels having a size about 10–30 $\mu$m in the lesion plane. The CCD camera 16 from Electrim, Inc., has 753×488 pixels. The spatial resolution with such a camera is approximately 21×24 $\mu$m at the lesion plane. Digital images of lesions obtained with this imaging system were used to classify lesions as malignant or benign, and to characterize lesions as invasive or non-invasive, as described further, below. The Electrim, Inc., CCD camera has 16 has rectangular pixels. A CCD camera with square pixels would simplify the calculating procedures.

Alternatively, a 3-chip CCD camera 20, indicated in phantom in FIG. 1c, may be used to reimage the slides of the region of interest. The CCD camera 20 provides digitized images for subsequent analysis by the computer 12. Broad bandpass filters, which are part of the CCD camera 20, produce a representation of the lesion as a set of three narrowband images. The filters are typically in accordance with CIE Standard Observer, wherein the bandwidths are broad.

Figure 2:
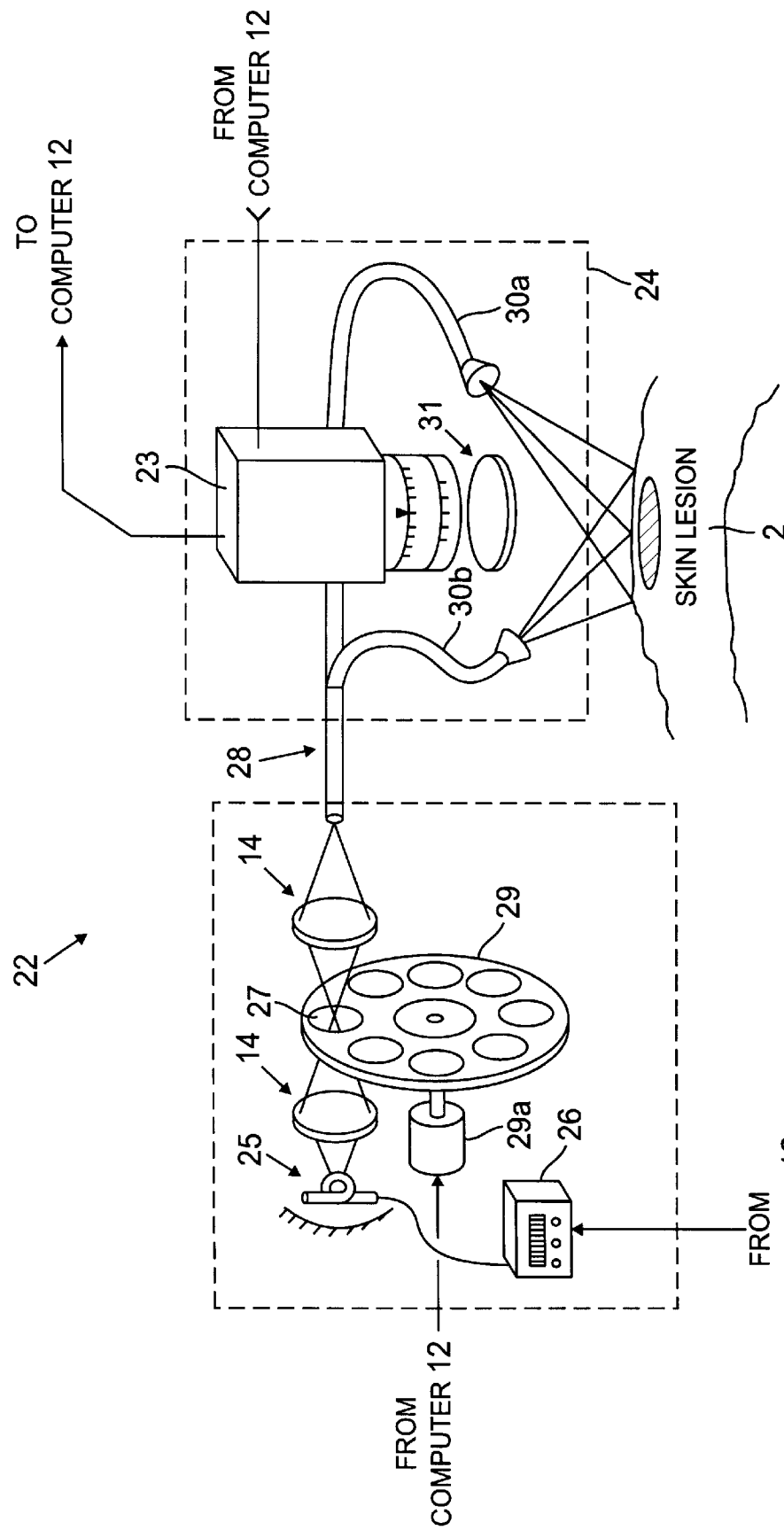
FIG. 2 is a schematic illustration of preferred illumination and imaging portions of a computer controlled imaging system for direct imaging of a lesion.

FIG. 2 is a schematic illustration of the illumination and imaging portions of a preferred computer controlled imaging system 22 in accordance with the present invention, for imaging a region of interest of skin including a lesion. The electronic camera 23 may be a 10-bit monochromatic electronic CCD camera 23, such as the Xillix Model 1400, available from Xillix Technologies Corp., Canada. The Xillix camera is equipped with wide band, low distortion foreoptics, such as the XJP 1.9/0501, available from Jos. Schneider Werke, Germany. The lower distortion fore optics and the camera minimize chromatic aberrations of the optical system over the "multispectral" sequence of exposures, enabling registration of images with sub-pixel accuracy, over the entire field of view.

To ensure repeatability of imaging conditions and to minimize required intervention by the operator, it is preferred that the system be operated at a preset f/stop. For cameras such as the Xillix Model 1400, exposure times are preferably controlled by the computer 12 through an electromechanical shutter that can operate reliably between minimum and maximum exposure times $t_{min}$ and $t_{max}$.

The imaging system provides low-noise, high-resolution digital images at high data transfer rates, with low distortion imaging over the entire range of wavelengths covered by the collection of filters. The Xillix, discussed above, has a resolution at the skin surface of about 20 microns per pixel.

The CCD camera 23 is preferably contained in a hand-held unit, represented schematically as box 24. The illuminator source 25 is a tungsten-halogen lamp whose intensity is controlled by a light-stabilized power supply 26 whose setting is automatically adjusted by the computer 12. A 150 watt lamp, such as the Phillips EJA, available from Phillips Electronics North America Corporation, N.Y., may be used, for example. The output of the lamp 25 is white light A narrowband filter 27 is provided between the source and an optical fiber 28. A plurality of narrowband filters, each one corresponding to a different spectral wavelength band, are mounted on a filter wheel 29. Preferred filter bandwidths are listed in Table 1, below. The filter wheel 29, which is driven by a stepping motor 29a, advances each filter to its proper position between the lamp 25 and the optical fiber 28, and holds each filter in position for a sufficient period of time. The computer 12 controls the motor 29a. More or fewer filters may be used. Appropriate lenses 14 are provided between the lamp 25 and the filter 27, and between the filter 27 and the optical fibers 28, as well. One or more fiber illuminators are provided for conveying the light from the source to the lesion. Two such illuminators 30a, 30b are shown in FIG. 2 for simplicity. Although the fiber illuminator illustrated is a bifurcated pair, a ring illuminator which provides more nearly uniform illumination at the skin surface, is preferred. An angle of illumination of about 20° is also preferred. A Fostec Model A0603 available from Fostec, Inc., N.Y., may be used, for example.

The hand-held portion of the system 24 of FIG. 2, which includes the camera 23, may be mounted on a cantilevered arm (not shown) that can be locked into position.

The digital signals making up each of the digital images output from the camera 23 are provided to the computer 12. The computer 12 conducts image processing procedures on the digital images to calibrate the images, and to objectively segment, estimate parameters, and classify the lesions based on the estimated parameters. Operator judgment is not required at any point in the process.

Control is maintained by the computer 12 over source intensity, filter position, and such camera settings as shutter timing, through the digital interface 12a. Key control parameters are empirically chosen on the basis of feedback from histograms of trial images. The intensity of the lamp 25 may be maintained at a stable value, commensurate with the 10-bit dynamic range of the camera 26, by monitoring a secondary light source, connected electrically in series with the primary light source 25. The light output from the secondary source is monitored by a light sensor that is optically isolated from light reflections associated with the primary source. Such reflections may be caused by the filters that are located on the filter wheel, or from the housing of the primary light source. This method provides optical feedback which is sensitive to changes in light intensity caused by changes in lamp lead resistance, for example, while it is insensitive to the variable amounts of light reflected from the filters, for example. By means of a closed control loop, the optical feedback from the secondary source is used to maintain long-term constant light output from the primary source.

The apparatus of FIG. 2 can be used for either clinical imaging of the skin, wherein the skin is imaged directly, dermoscopic imaging, wherein a layer of oil is provided over the skin and a layer of glass placed over the oil layer, or polarized imaging, where a polarizer 31 is added to minimize specular reflection as shown in FIG. 2. In dermoscopic imaging, the index-matching oil sufficiently reduces the specular reflection to avoid the need for a polarizer.

Instead of being positioned between the light source 25 and the optical fiber 28, the narrow bandpass filters 27 may be placed between the skin and the CCD camera 23 to filter the light reflected, scattered and radiated from the skin 2.

The front end of the system preferably consists of a flat glass plate (not shown) for being placed over the skin. Light pressure is applied through the glass, onto the skin, throughout the imaging process. This helps to stabilize the region of interest against unwanted motion which could blur an image or which could lead to spatial misregistration between images obtained in different filter bandpasses.

The preferred filters 27 for lesion imaging with a tungsten-halogen white light source 25 have the center wavelengths $\lambda_i$ and bandwidths (FWHM) listed in Table 1, for i=1,2, ..., M, M=10, wherein the bands are labeled by j=i−1=0,1, ... M−1. Such filters are available, for example, from Intor, Inc., Tucson, Ariz. In each band, the exposure time is preferably selected to avoid saturation of the detector elements of the CCD camera 23, as well as to maximize the linear dynamic range over which the image data are recorded. These exposure times should be constrained to be within limits $t_{min}$ and $t_{max}$ which are related to the electro-mechanical design of the shutter, optical throughput of the camera 23, and avoidance of image blur associated with motion during the exposure sequence. Suitable values of $t_{min}$ and $t_{max}$ could be 10 ms and 550 ms, respectively, for example. The choice of center wavelength and FWHM for the filter channels, as well as the corresponding exposure times, should preferably also take into account the following considerations:

(a) The center wavelength and FWHM for at least two channels should be chosen so that characteristic absorption lines can be differentiated, such as those associated with melanin and hemoglobin;

(b) For a given set of center wavelengths, there are upper limits on the associated bandwidths if spectral independence of data in different channels is to be maintained, as illustrated in FIG. 1(a);

(c) Bandpasses should be chosen in the red, green and blue portions of the spectrum which enable "true-color" reconstruction of skin images that are suitable for visualization by clinicians;

(d) The need for high signal-to-noise ratio in each image sets practical lower limits on the product of exposure time and filter bandwidth, especially at short wavelengths, where detector response falls off and lesion reflectance is low; and (e) The total time taken to acquire the images in all filter bands is preferably less than about three minutes, to minimize patient discomfort and possible motion.

Based on considerations (d) and (e) above, and also taking into account the varying spectral reflectances of skin of different colors, the exposure times in each filter channel are preferably adjustable, with settings based on the dynamic range achieved on an empirical basis, with trial images. In this manner, both dynamic range and signal-to-noise ratio can be maximized for each filter channel. The preferred method is to choose $t_{expi}$ by iteration, based on intensity histograms of images of the skin obtained with trial exposures at each wavelength band. The histograms are analyzed to determine the number of pixels at the saturation intensity level, $I_{sat}=2^b-1$ (1023 for b=10 bits). The exposure time is decreased if the number of saturated pixels exceeds a predetermined amount, such as 0.01% of the total. Conversely, to maintain high signal-to-noise ratio, the exposure time is increased if a predetermined percentile in the histogram, 99.9%, for example, is reached at less than a preset threshold, such as 99.5% of $I_{sat}$. The iteration process typically converges after two or three trials.

The preferred exposure times at each wavelength for imaging skin of different colors to classify melanomas are listed in Table 1, for the embodiment of FIG. 2 with 10 filters. It has been found that for the blue channel centered at 450 nm, the optimal exposure time for dark skin is 273 ms, which is more than double the optimal 107 ms exposure time for light skin. On the other hand; in the near infrared channel centered at 780 nm, the exposure times listed are much shorter, between 24 and 35 ms, and vary relatively little with skin type. The optimal exposure time for dark skin in the deep blue channel at 430 nm is at $t_{max}$=550 ms, due to the low skin reflectance and relatively low optical throughput of the system at this short wavelength. Even with an exposure time this long, therefore, the image is less than fully exposed. Greater throughput at this wavelength could be achieved, at the expense of poorer response in the infrared.

In Table 1, the FWHM at 450 nm, is 100 nm, which is much broader than for other wavelengths. It has been found that where images are desired for visual analysis as well as computer processing, the broad wavelength band at 450 nm more closely matches the blue response of the human eye and is therefore preferred. In addition, the broad wavelength band provides data at a higher signal-to-noise ratio.

Table 1 appears below:

| | Optimal Exposure Times (msec) vs. Skin Color | | | | | |
|---|---|---|---|---|---|---|
| Filter Number (j = i − l) | Center Wavelength (nm) | Filter FWHM (nm) | Very Light Skin | Medium Skin | Tan Skin | Dark Skin |
| 0 | 430 | 60 | 405.2 | 436.5 | 484.4 | 550.0 |
| 9 | 450 | 100 | 106.8 | 124.9 | 156.1 | 273.3 |
| 1 | 500 | 40 | 56.4 | 62.9 | 88.7 | 130.7 |
| 2 | 550 | 10 | 44.2 | 50.4 | 71.3 | 92.9 |
| 3 | 600 | 10 | 19.1 | 24.0 | 29.6 | 39.2 |
| 8 | 650 | 10 | 74.5 | 92.3 | 104.9 | 132.0 |
| 4 | 700 | 10 | 71.6 | 86.0 | 98.0 | 114.4 |
| 5 | 780 | 30 | 25.8 | 29.1 | 34.9 | 23.6 |
| 6 | 880 | 50 | 34.1 | 38.6 | 44.8 | 46.1 |
| 7 | 950 | 60 | 161.1 | 187.6 | 205.8 | 212.0 |

Tables similar to Table 1 can be readily constructed based on experimental results for other applications, where other spectral bands may be better suited. For example, in the analysis of wound healing, the ability to distinguish oxygenated from deoxygenated blood would be desirable. In addition, the wavelengths and exposure times in Table 1 reflect a balance between the best results for subsequent analysis of the images by a computer, and the best results for visual observation of the images. If visual observation is not necessary, other wavelength bands and exposure times may be used.

Figure 3A:
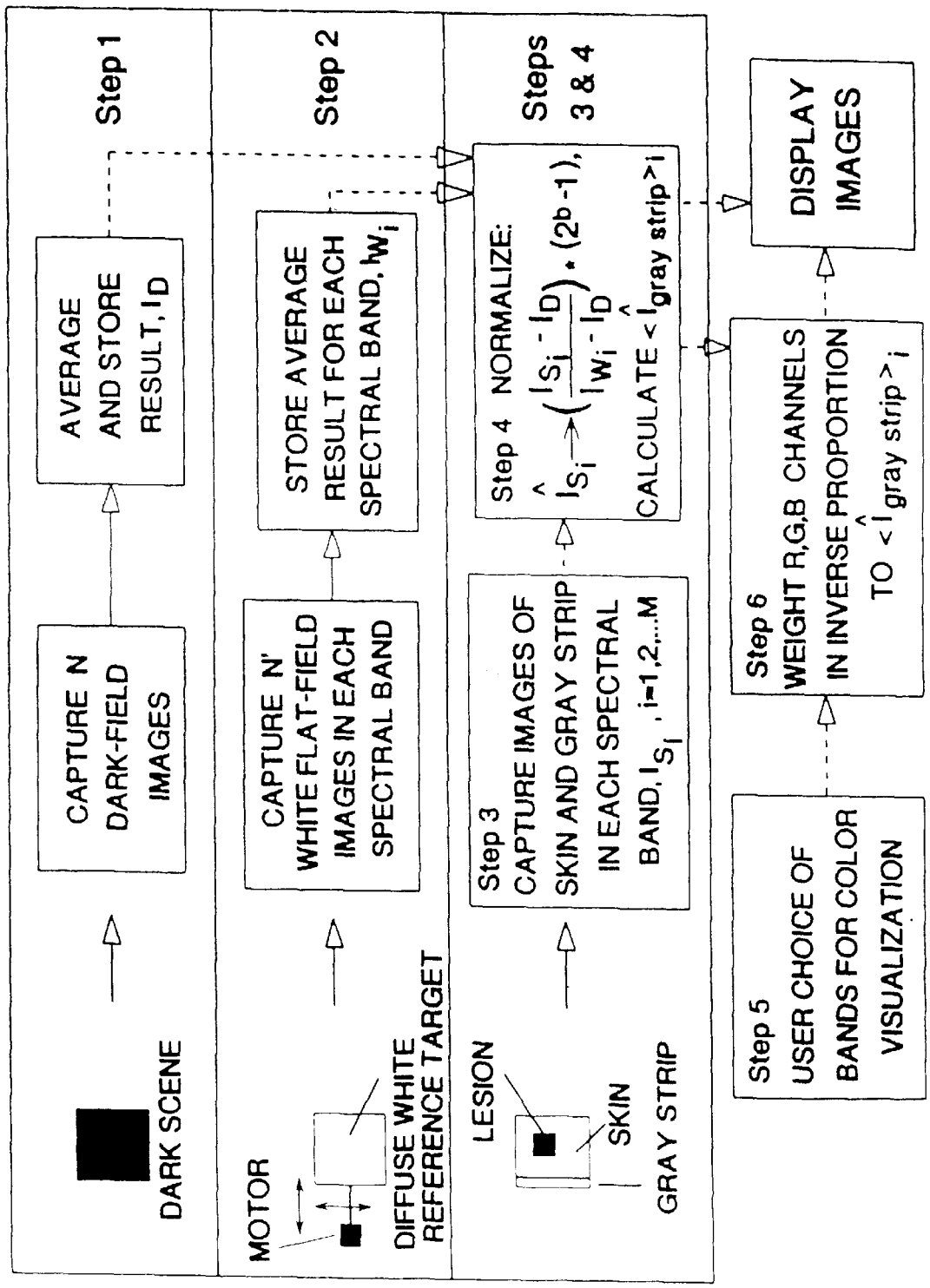
FIG. 3(a) is a flow chart of a calibration procedure for use with the present invention.

FIG. 3(a) describes how the systems and methods of the present invention provide for calibration of the recorded images. The calibration procedure permits 10-bit image data to be recorded over a large linear dynamic range in each spectral band, independent of skin type. The recorded images can also be standardized for diffuse spectral reflectance. Consistent measures of reflectance ratios in different spectral bands can therefore be obtained, despite variations in illumination pattern with wavelength, changes in the position of the illuminator, or aging of the lamp, for example.

First, the effects of dark current and "fixed pattern noise" are removed in Step 1. N images are recorded by the camera without illumination. Preferably 8 such dark images are recorded. The average of these N dark images, ID is calculated and stored in the computer 12.

Second, spatial inhomogeneities in the illumination and in the response associated with each CCD pixel are removed in Step 2. A sequence of N' images of an illuminated flat, diffuse reflectance standard, such as a white Spectralon® target (R>99%) recorded. As above, N' is preferably 8. The N' images are recorded at each wavelength band. To average over local inhomogeneities in the reflectance standard, the target is moved continuously during the integration time and between exposures. A small motor, such as a reciprocating motor, may be used. The integration time and/or lamp intensity are adjusted by the computer 12 at each wavelength band until negligibly few of the pixels are at or just below an intensity level corresponding to saturation. These N' "flat-field" images are averaged to reduce the effect of spatial non-uniformities in the reflectance standard, as well as to improve the detection signal-to-noise ratio. The resulting averages are stored in the computer as $I_{wi}$, where i=1, 2, . . . M.

Next, monochromatic "raw data" images of the skin, $I_{si}$, are captured by the camera and digitally acquired by the computer 12 within each filter passband, i=1,2, . . . M. If dermoscopic imaging is used, where a thin layer of mineral oil is spread between the skin and a cover glass is fixed in position in front of the camera, each image of the skin preferably contains an image of a narrow strip of oil-free, diffusely reflecting gray material, held in place on the inside surface of the cover glass, and located along one edge of the field of view. The material may be cut out of a Kodak "18% gray" card. Dermoscopic imaging is preferred for melanocytic lesions. The alternative clinical imaging mode is preferred for the imaging of wounds and burns because contact with the wound or burn by a cover glass is not desired. Although FIG. 2 indicates a lesion present on the skin 2, it will be readily understood that the same method will apply when a wound or burn is present, instead. In the clinical imaging mode, it is preferable to reduce specular reflections by employing the polarizer 31, as indicated in FIG. 2.

In either the dermoscopic or clinical imaging techniques, a fourth step is preferably provided, in which the raw data is compensated for dark current and fixed pattern noise and then normalized to the flat-field images. The dark-field compensation is performed by subtracting the stored average dark image $I_D$ both from the flat-field image $I_{wi}$ and from the raw data image $I_{si}$. The ratio of the results of these subtractions is then taken. This standardizes the dark-corrected raw data to the flat-field image, compensating for spatially varying illumination and pixel-to-pixel response variations. After the ratio is taken, the result is standardized to the maximum level, $2^b-1$ which equals 1023 where b=10 in a 10-bit data representation. The normalization process thus converts the image of the skin and the gray strip into a standardized diffuse reflectance map, with the result preserving a large linear recording dynamic range. In FIG. 3(a), the dark-field corrected and flat-field-normalized images, also referred to as "flat-field-calibrated" images, are denoted as $I_{si}$. In any image, standardization to maximum level can be reinterpreted directly in terms of equivalent diffuse reflectance on the basis of the average gray level over the image of the gray strip, $<I\text{gray strip}>_i$ and the measured average diffuse reflectance of the gray strip, which is approximately 0.2 and varies in a known and repeatable manner with wavelength.

Preferably, the average image intensity in the gray-strip region is also used to calculate weighting factors for combining three or more monochromatic images to provide "true-color" visualizations of lesion images on the computer 12 and display 19. This is preferably accomplished in Step 5, where the user selects the spectral bands to be used in the color visualization. Step 5 can take place prior to the imaging session. Four bands are currently preferred for such visualization. Filter bands j=3 and 8, in a 3:2 ratio, for the red (R) channel, filter band j=2 for the green (G) channel, and filter band j=9 for the blue (B) channel, in Table 1. As indicated in Step 6 of FIG. 3(a), the relative weights applied to the R:G:B channels are preferably inversely proportional to $<I\text{gray strip}>_i$ the average intensity over the portion occupied by the gray strip area in each image. This procedure tends to reconstruct the hues and saturations in the original scene to within accuracy limits associated with response nonlinearities of the display 19. To minimize the effects of such nonlinearities with display monitors such as the Sony Model GDM-175E1 Multiscan monitor, for example, the viewer may prefer to adjust the maximum brightness in the image to correspond to the maximum image intensity level of the monitor. A linear transformation step, which can be readily accomplished by commercial software such as Adobe Photoshop, may be used. If the digital images are derived from photographic slides, as in the embodiment of FIG. 1(c), steps 5 and 6 are not necessary.

As indicated by dashed lines in FIG. 3(a), either the normalized monochromatic images resulting from Step 4 or the color visualization provided from Step 6 can be displayed on the display 19. Any or all of the monochromatic raw images could be displayed as well.

Figure 3B:
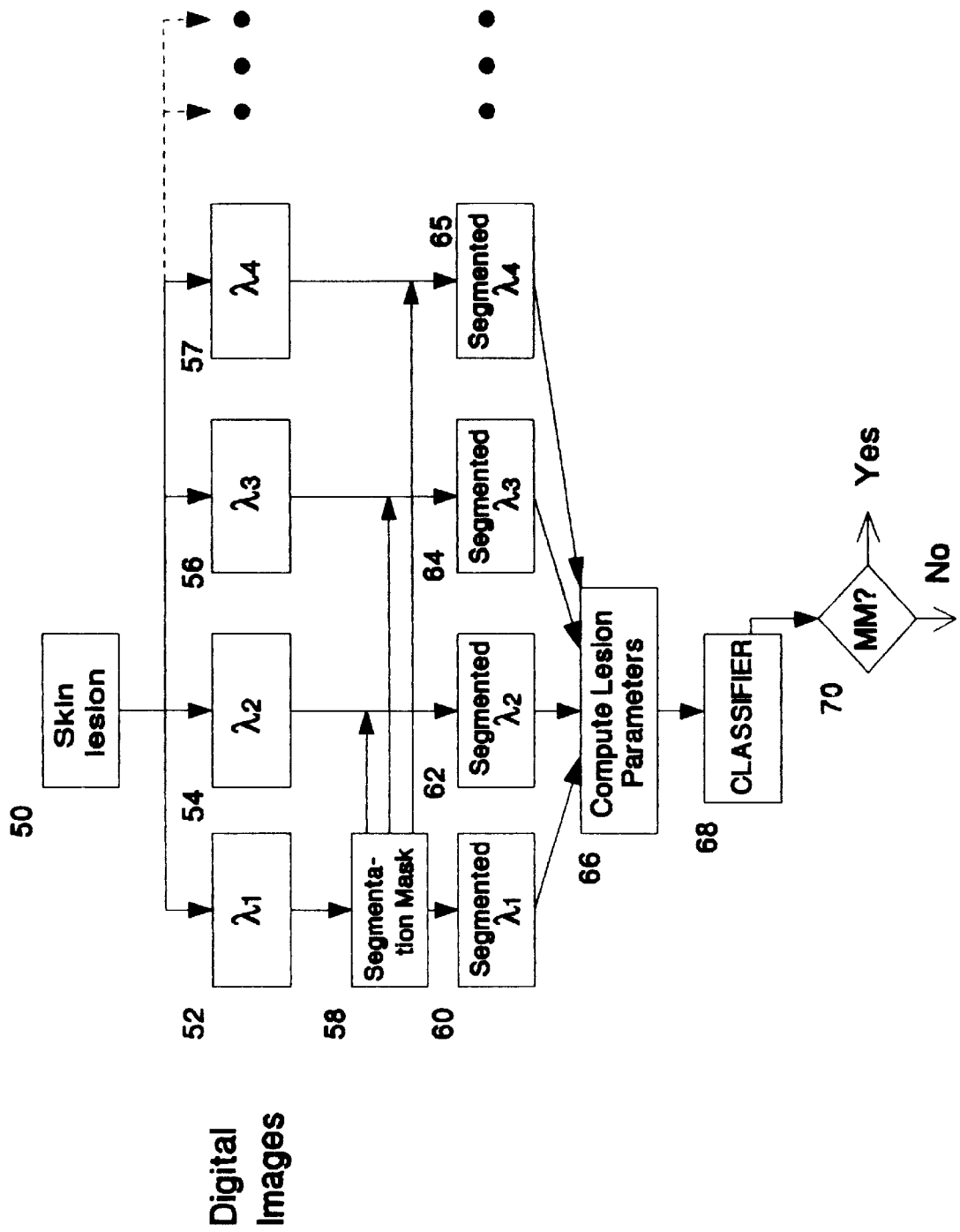
FIG. 3(b) is a flow chart of a method of processing images for classifying lesions as malignant or benign, in accordance with the present invention.

FIG. 3(b) is a flow chart of a preferred method of processing images according to the present invention for characterizing the condition of a region of interest of the skin of a subject which includes a skin lesion. A skin lesion is selected at Step 50. Digital images of the lesions illuminated by light filtered at the desired wavelengths of $\lambda_1-\lambda_4$. . . , are digitally recorded in Steps 52, 54, 56 and 57. . . , as described above. Each of these digital images is processed separately. In Step 58, the image taken at the lowest wavelength band is used to create a mask for segmentation. At Steps 60, 62, 64, 65 . . . , each of the images of the lesion that correspond to different wavelengths are segmented by means of the segmentation mask obtained at Step 58. Lesion parameters are computed from each of the segmented images, in Step 66. Lesion parameters found to be useful for classifying and characterizing the lesion and statistical methods for computing the estimated values of the parameters, are discussed further, below. The estimated values of the parameters are provided to a linear classifier in Step 68. The linear classifier employs a linearly weighted sum of the individual parameters to derive a value used to classify the lesion as malignant or benign. A non-linear classifier such as a Gaussian quadratic classifier or an artificial neural-net classifier, each employing a suitable defined merit function, may be used as well. In either case, the numerical value produced by the classifier is subjected to a threshold test at Step 100, such that if the test is passed, the lesion is suspected to be malignant melanoma. If the test is failed, the lesion is declared not to be melanoma. The lesion could also be characterized as invasive or non-invasive with a different classifier.

I. SEGMENTATION

The segmentation algorithms will now be described. The function of the segmentation algorithms is to discriminate between the lesion and normal skin in the field-of-view of the imaging device. This is a complex function since not only is the lesion appearance highly variable but so is the appearance of healthy skin due, for example, to the presence of blotches, hair, wrinkles, etc. The automatic algorithm described here is based on the images in the blue spectral band, from about 400 nanometers (nm) to 500 nm. This spectral band was selected because melanin absorption increases rapidly as the wavelength decreases. While the use of ultraviolet radiation could be advantageous, since ultraviolet radiation is carcinogenic, only low doses can be used.

Segmentation in blue consists of several automatic steps:

Location of major peaks in the histogram

Figure 4A:
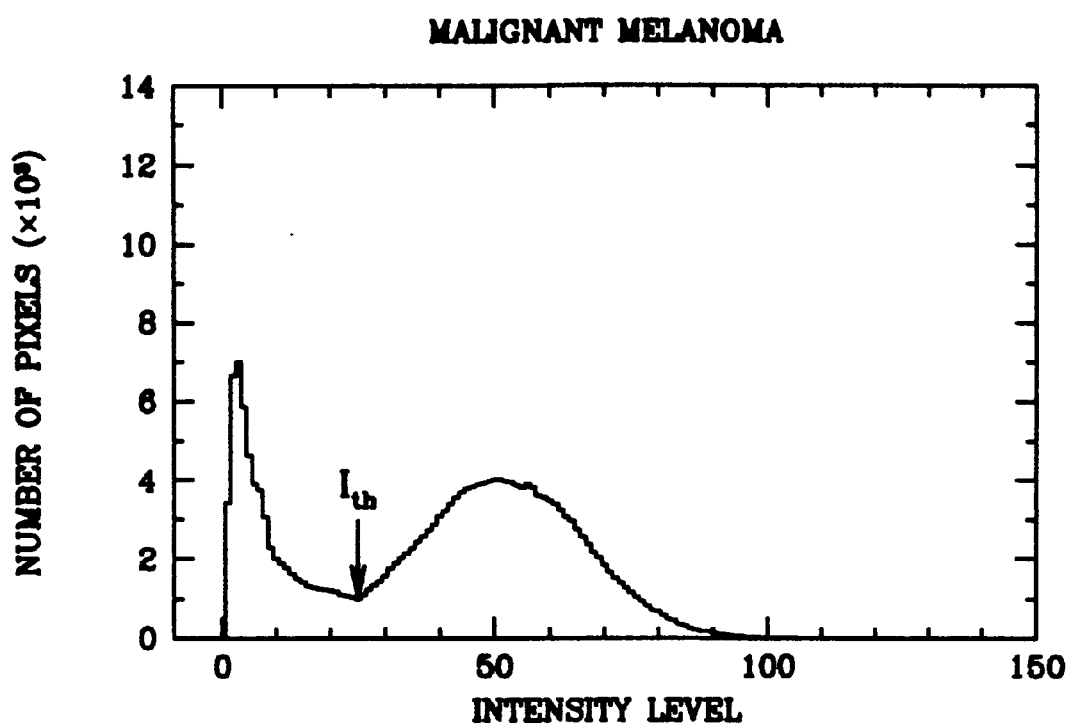
FIGS. 4(a) and 4(b) are histograms of a malignant melanoma and of an atypical melanocytic nevus, respectively, showing two peaks in each histogram.

First, the histogram of intensity levels in the whole image is determined. Then, given a sliding window with the range of $(2I_r+1)$ intensity levels, the number of peaks $N_p$ in the histogram over that range is determined. If $N_p<2$, the range is decreased by two levels and if $N_p>3$, the range is increased by two levels and the process is repeated until $N_p=2$ or 3. For most of the images in the data base used in this study, there are two major peaks in the histogram. Examples of such histograms are shown in FIG. 4(a) for a malignant melanoma and in FIG. 4(b) for an atypical melanocytic nevus. The lesions correspond to the lower intensity peak, since it is darker than the surrounding skin due to strong absorption by melanin at 400 nm. However, some lesions are quite inhomogeneous, and the automatic procedure described can find 3 major peaks, as illustrated in FIGS. 5(a) and 5(b).

Location of the intensity threshold

Figure 4B:
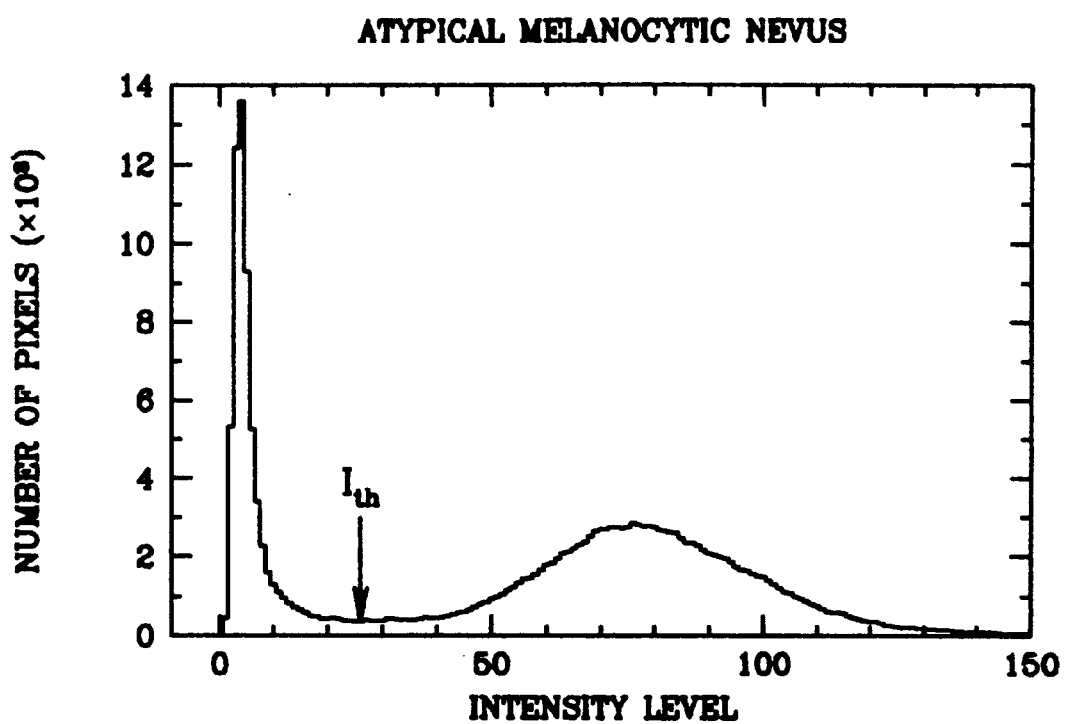
Figure 5A:
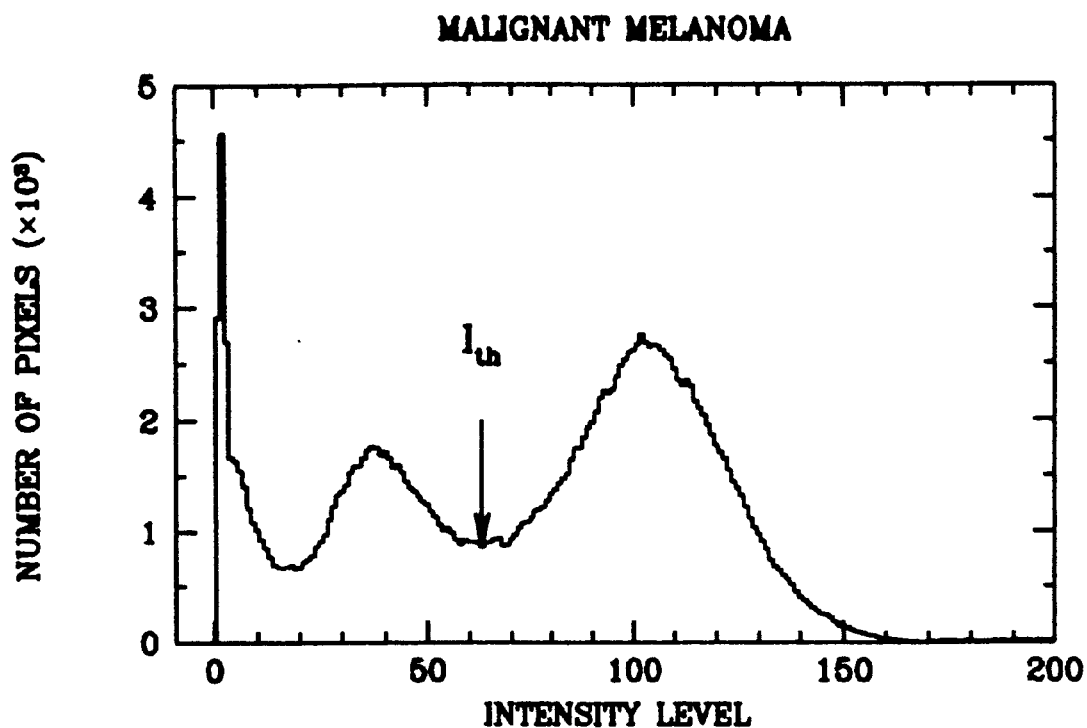
FIGS. 5(a) and 5(b) are histograms of another malignant melanoma and another atypical melanocytic nevus, respectively, showing three or more peaks in each histogram.
Figure 5B:
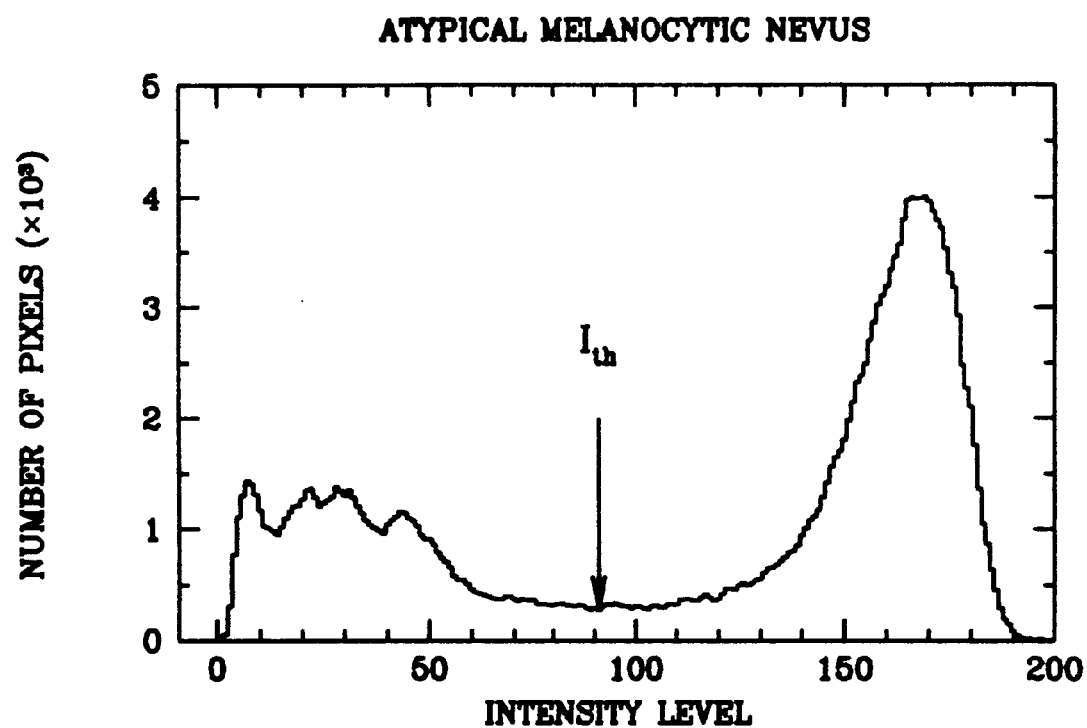

If two major peaks are found in the intensity histogram, then the threshold value $I_{th}$ is selected to be at the histogram minimum between these two peaks, as indicated in FIGS. 4(a) and 4(b). In the case of three peaks, it has been found that, if the middle peak is closer to the lowest intensity peak, the threshold value is at the minimum between the middle and the highest intensity peak. If the middle peak is closer to the highest intensity peak, then the threshold value is at the minimum between the middle and the lowest intensity peak, as shown in FIGS. 5(a) and 5(b).

Iterative thresholding of the image

The next step in image segmentation is iterative thresholding of the images. Given the intensity threshold value, image thresholding has been typically accomplished as follows. The intensity I(x,y) of a pixel at location (x,y) is set to zero if it exceeds $I_{th}$, i.e., $$I_L(x, y) = \begin{cases} I(x, y), & \text{if } I(x, y) < I_{th}; \\ 0, & \text{otherwise.} \end{cases} \quad (1)$$

Figure 6A:
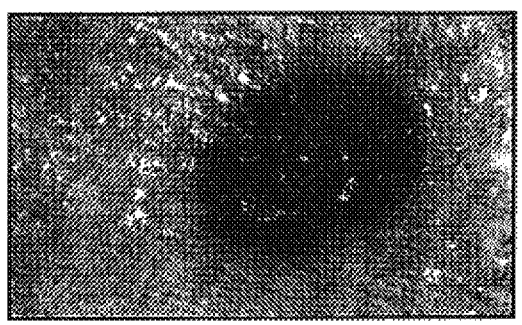
FIGS. 6(a) and 6(d) are digital images in the blue spectral band of another malignant melanoma and another atypical melanocytic nevus, respectively.
Figure 6D:
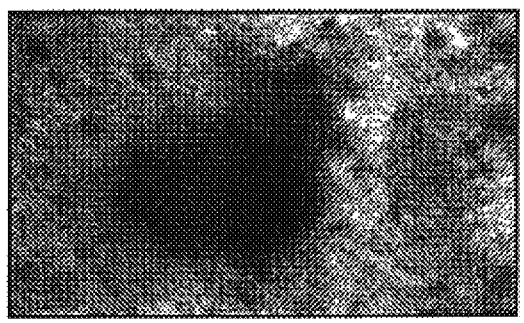
Figure 6B:
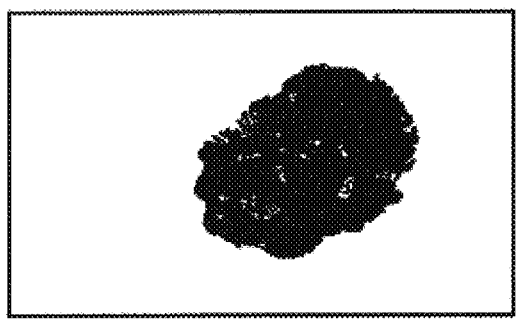
FIGS. 6(b) and 6(e) are digital images of the images of FIGS. 6(a) and 6(d) respectively, after thresholding.
Figure 6E:
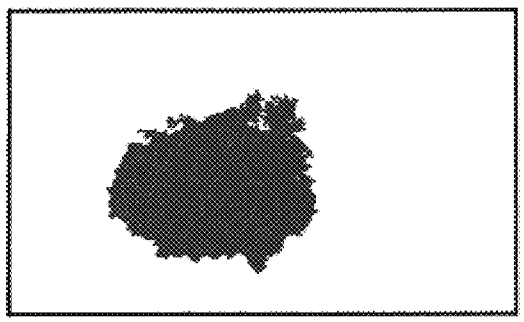

FIGS. 6(a) and 6(d) are examples of digital images of malignant melanoma and atypical melanocytic nevus in the blue spectral band, respectively. FIGS. 6(b) and 6(e) are images resulting from the direct thresholding as in Eq. (1). As shown in FIGS. 6(b) and 6(e), "holes" can appear within the lesion. Therefore, an iterative approach is preferably used. First, the intensity of pixels at the image edges is set to zero. Then as each iteration proceeds, the intensity I(x,y) of a pixel at location (x,y) is set to zero if it exceeds $I_{th}$ and at least one of its nearest neighbors has zero intensity, i.e., $$I_L(x, y) = \begin{cases} 0, & \text{if } I(x, y) \geq I_{th} \text{ and } N_{nn} = 0; \\ I(x, y), & \text{otherwise,} \end{cases} \quad (2)$$

where $$N_{nn} = \min[I(x-1,y), I(x+1,y), I(x,y-1), I(x,y+1),]. \quad (3)$$

Figure 6C:
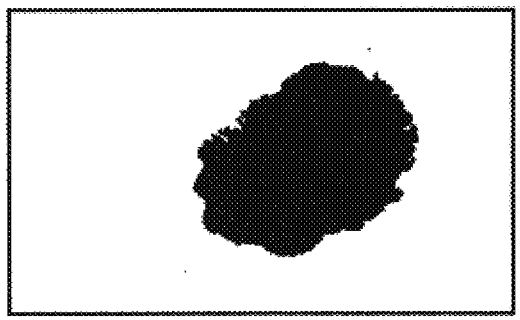
FIGS. 6(c) and 6(f) are digital images of the images of FIGS. 6(a) and 6(d), respectively, after iterative thresholding.
Figure 6F:
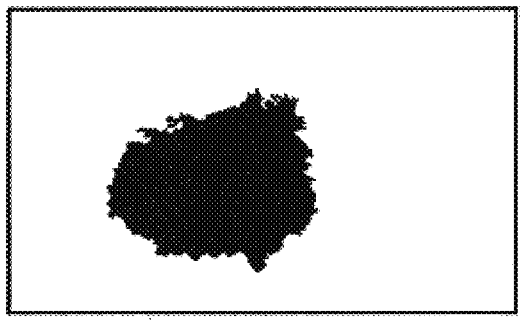

This procedure is iterated until there are no pixels with $I(x,y) \geq I_{th}$, and a nearest neighbor with zero intensity. Typically, only a few iterations are required to complete this step. The resulting images are shown in FIGS. 6(c) and 6(f).

Figure 7A:
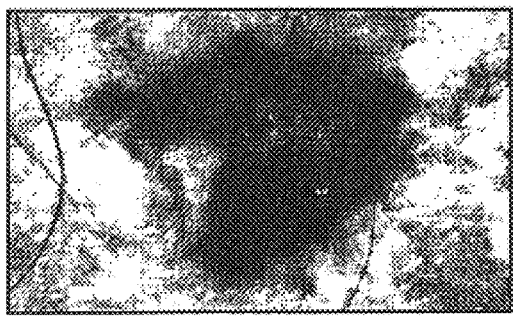
FIGS. 7(a) and 7(d) are digital images in the blue spectral band of another malignant melanoma and another atypical melanocytic nevus.
Figure 7D:
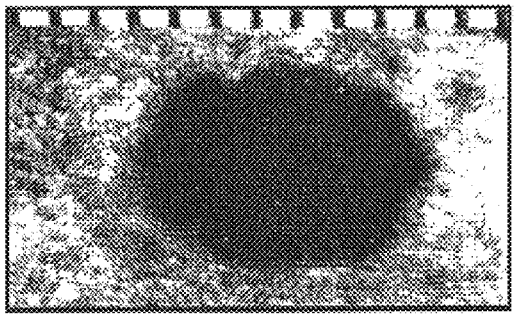
Figure 7B:
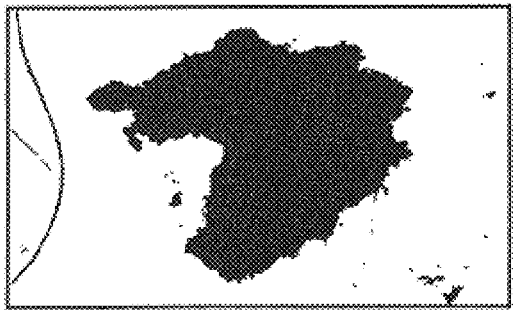
FIGS. 7(b) and 7(e) are digital images of FIGS. 7(a) and 7(d), respectively, resulting from iterative processing and showing dark blobs outside the lesion area.
Figure 7E:
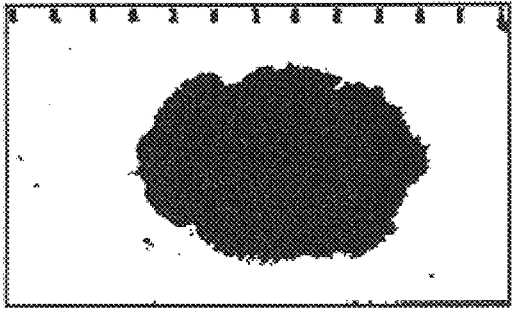

FIGS. 7(a) and 7(d) are other examples of digital images of malignant melanoma and atypical melanocytic nevus, respectively. FIGS. 7(b) and 7(e) are images resulting from the iterative thresholding described above. Various dark blobs are seen in the images outside of the lesion area. These are removed in the following step.

Image cleaning

Some of the blobs in the thresholded images arise naturally due either to dark spots on the normal skin or to hair as in FIG. 7(b). Others are artifacts such as the film edge at the top of the nevus image in FIG. 7(e), or dark bands at the image edges from the slide mounts. These bands are removed by automatically testing for their presence and then setting the intensity of appropriate pixels to zero. The remaining blobs could also be removed by determining the overall number and size, i.e., number of pixels, of connected blobs, and then setting to zero the intensity of pixels belonging to the small ones. However, since the size of some lesions exceeds 100,000 pixels, this would be computationally very intensive. Therefore, in practice, this step is preferably carried out as follows. First, perimeter pixels for all blobs in the image are located. The number of such pixels is typically less than 10,000. Then, each of these perimeter pixels is assigned to a unique blob and its size, the number of perimeter pixels in the blob, is determined. The intensities of pixels belonging to blobs of size less than 30% of the maximum size for that image are set to zero. This process is iterated until all the small blobs are removed. Typically less than 10 iterations are needed. The intensity of all the nonzero pixels is then set to 1. The resulting binary lesion mask has the following property:

$$I_B(x, y) = \begin{cases} 1, & \text{if pixel at } (x, y) \text{ belongs to lesion;} \\ 0, & \text{otherwise.} \end{cases} \quad (4)$$

Figure 7C:
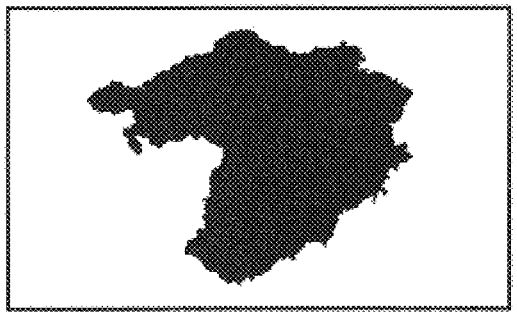
FIGS. 7(c) and 7(f) are digital image masks of FIGS. 7(b) and 7(d), respectively, resulting from image cleaning.
Figure 7F:
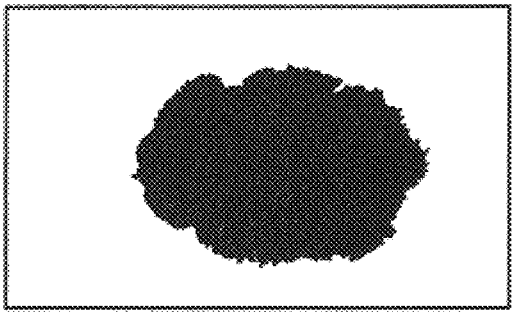

FIGS. 7c) and 7(f) illustrate the resulting lesion masks.

In the images illustrated in FIGS. 7(a) and 7(d), dark hairs were either absent or were not adjacent to the lesion. However, there are many images with prominent dark hair overlapping lesions. Segmentation of such images is described in the following section.

Segmentation of images in presence of hair

Figure 8A:
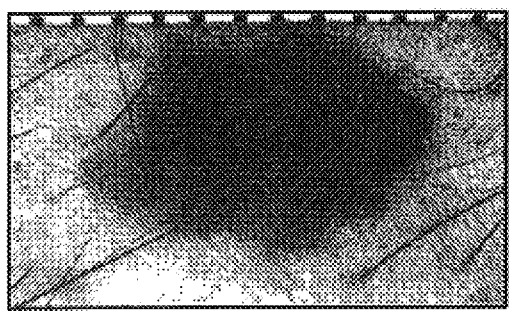
FIGS. 8(a) and 8(e) are digital images in the blue spectral band of another malignant melanoma and another atypical melanocytic nevus, respectively, showing hair.
Figure 8E:
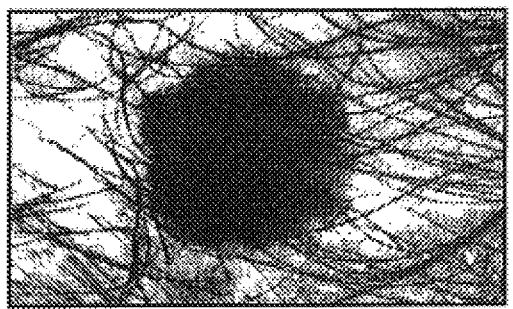
Figure 8B:
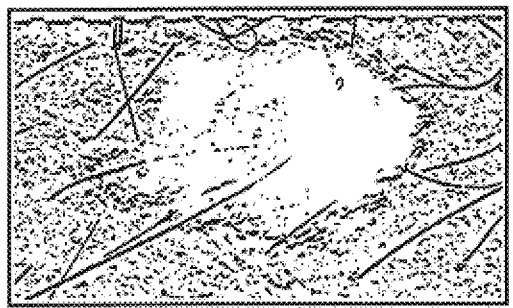
FIGS. 8(b) and 8(f) are reverse intensity contrast images of the lesions of FIGS. 8(a) and 8(e), respectively.
Figure 8F:
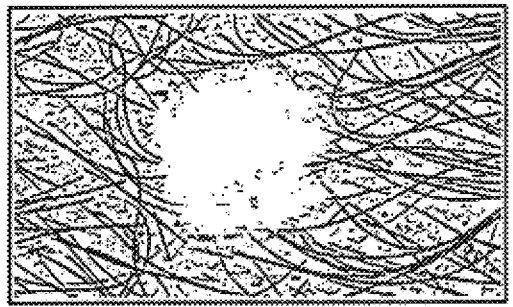

FIGS. 8(a) and 8(e) are examples of lesion images with hair. Since the segmentation algorithm described in the previous section would leave some of these dark hairs connected to the lesion, images with hair require special preprocessing to allow for hair removal from the normal skin. Since hair is a problem because of its high contrast with respect to the normal skin in the blue, a spatial filter was designed to locate hairs. This filter, shown in FIG. 9, is magnification dependent. It is applied to every pixel of the original image and the result is thresholded at the 5% of maximum value in the whole filtered image. The filtered images are shown in FIGS. 8(b) and 8(f) in reverse intensity contrast, wherein bright features are dark. Hairs are clearly located in the filtered images. It should be noted that the lesion interior is almost entirely blank, indicating poor contrast between hair and lesion.

Hairs are removed by an averaging process. For every non-zero pixel at (x,y) in the filtered image one finds the locations of 4 nearest pixels $(x_l, y)$, $(x_u, y)$, $(x, y_l)$, $(x, y_u)$ (where $x_l < x < x_u$ and $y_l < y < y_u$) with zero intensity. Then the intensity of every pixel in the original image that has non-zero intensity in the filtered image is replaced as follows:

$$I_n(x, y) = \frac{1}{12}\sum_{k=1}^{3}[I(x_u+k, y) + I(x_l-k, y) + I(x, y_u+k) + I(x, y_l-k)]. \quad (5)$$

Figure 8C:
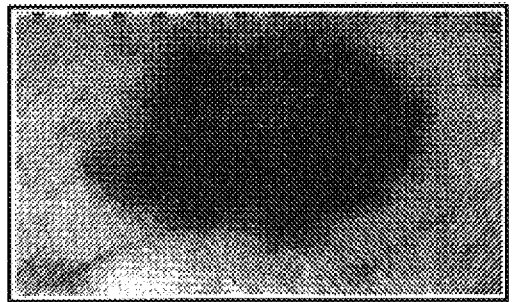
FIGS. 8(c) and 8(g) are digital images resulting from an averaging process applied to the images of FIGS. 8(a) and 8(b), to remove hair.
Figure 8G:
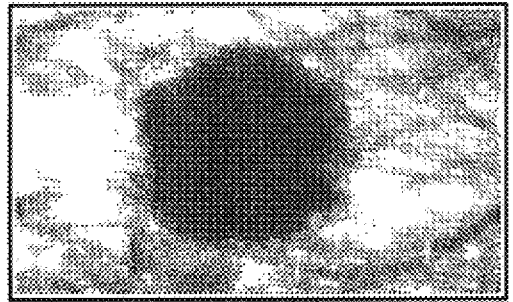
Figure 8D:
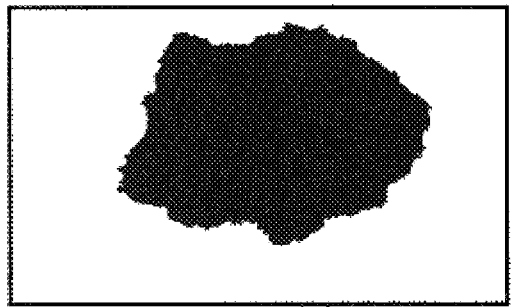
FIGS. 8(d) and 8(h) are binary lesion masks resulting from the segmentation of the images of FIGS. 8(c) and 8(g), respectively.
Figure 8H:
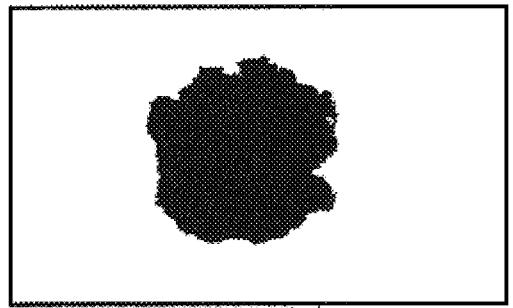
Figure 10A:
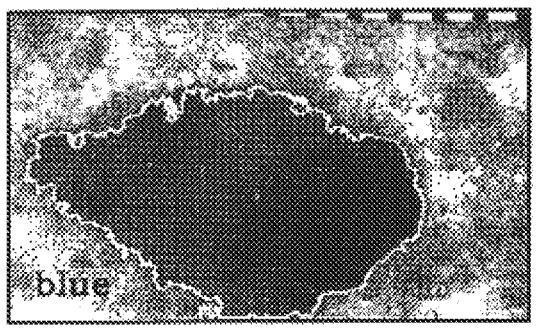
FIGS. 10(a)–10(c) are segmented digital images in the blue, green and red spectral bands, of the malignant melanoma whose histogram is shown in FIG. 5(a)
Figure 10D:
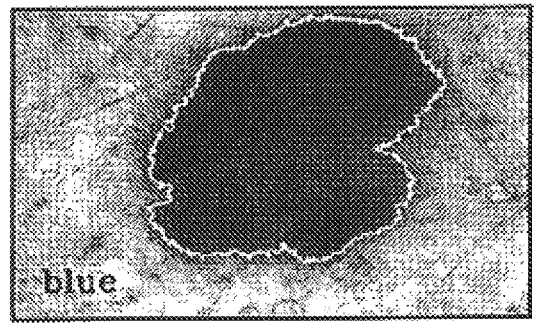
FIGS. 10(d)–10(f) are segmented digital images in the blue, green and red spectral bands, of an atypical melanocytic nevus whose histogram is shown in FIG. 5(b)
Figure 10B:
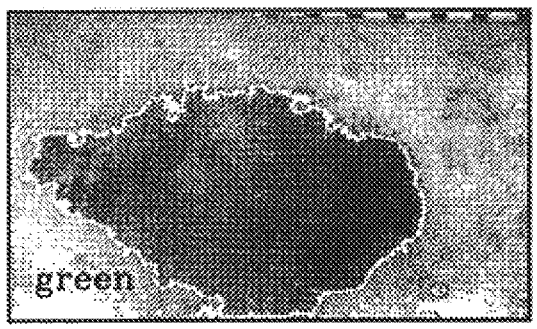
Figure 10E:
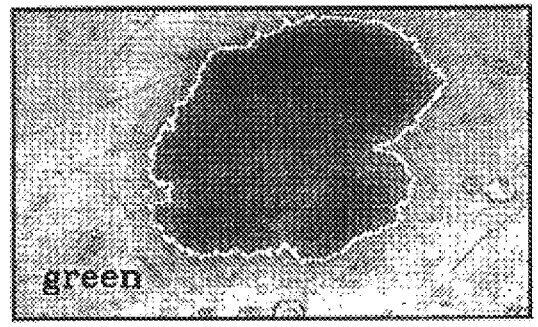
Figure 10C:
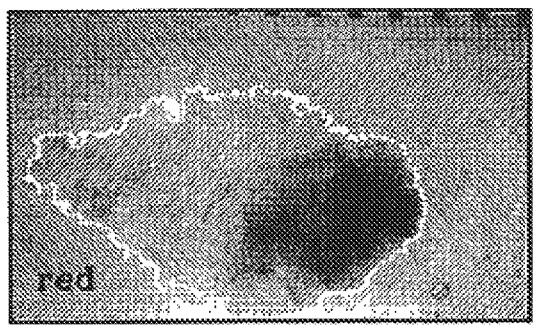
Figure 10F:
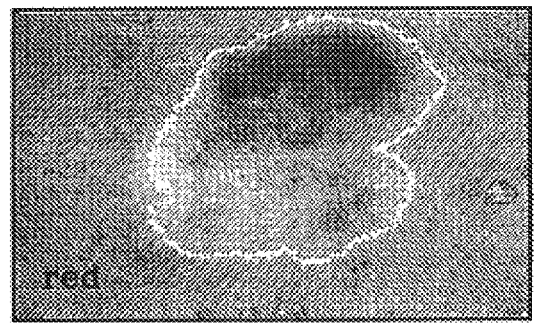

The images averaged in this way are shown in FIGS. 8(c) and 8(g). It is seen that the contrast between hairs and normal skin is considerably reduced in these images. After this preprocessing, the segmentation algorithm described in the previous section is applied to the averaged image. The final binary lesion masks are shown in FIGS. 8(d) and 8(h).

The preprocessing step described above may be used for all lesion images, regardless of the presence of hair, enabling fully automated lesion segmentation. However, since this requires more computation and causes some border blurring, the need for preprocessing due to the presence of dark hair is preferably indicated interactively by an operator, and images preprocessed only when necessary.

Segmentation of images in other spectral bands

Since melanin absorption is strongest in the shortest-wavelength band, the lesion area, which appears as a dark region in the image, appears largest in the blue spectral band. Since longer wavelength radiation penetrates deeper into skin, if the thickness of the melanin-containing layer compensates for the weak absorption, that part of the lesion will appear dark even in the red spectral band. For thick melanomas, with Breslow thickness greater than 1 mm, one expects dark lesions even m the infrared bands. This was observed, for example, by Marchesini et al., Photochemistry & Photobiology, "In vivo spectrophotometric evaluation of neoplastic and non-neoplastic skin pigmented lesions. III. CCD camera-based reflectance imaging," Vol. 62, 1995, pp. 151–154. However, for early malignant melanomas, with Breslow thickness less than 1 mm, great variability of images in the red spectral band has been found. There may be so little contrast between the lesion and the normal skin that direct segmentation is not possible. Therefore, segmentation of lesion images in all spectral bands with wavelength λ uses the binary lesion mask of Eq. (4), obtained in the shortest-wavelength band, here blue, i.e., $$I_L(x,y;\lambda) \equiv I(x,y;\lambda) \times I_B(x,y) \quad (6)$$

FIGS. 10(a)–10(f) are a series of images of the lesions, with their corresponding histograms shown in FIGS. 5(a) and 5(b), segmented in the blue, green, and red spectral bands, as indicated. The automatically determined lesion borders are superimposed on the original lesion images. The area of dark regions is largest in the blue.

II. LESION PARAMETER ESTIMATION

Objective and automatic lesion classification requires quantitative algorithms for lesion parameter estimation from their segmented images. Such parameters should be dimensionless, independent of lesion location and orientation in the image, and of the overall image brightness. It is convenient to separate the parameters used here into four broad classes: asymmetry, blotchiness, border, and texture. Parameters with the highest diagnostic accuracy for malignant melanoma are listed in FIG. 11, together with the values of diagnostic accuracy, sensitivity, and specificity, for a training set of images of 41 malignant melanomas and 104 atypical melanocytic nevi obtained with the imaging system described above, with respect to FIG. 1(a) wherein the monochrome camera 16 was used to digitize slides. The subscript r, g, or b refers to the red, green, or blue spectral band in which the parameter is evaluated. If additional spectral bands are used, then each of the parameters could be computed at the additional spectral bands, as well.

Specific algorithms for these parameters are described below. For simplicity it is assumed that the image pixels are square but the algorithms described below may be implemented for rectangular pixels as well.

Lesion Asymmetry

Asymmetry parameter

The lesion asymmetry parameter is based on moments of the intensity distribution. First, the lesion orientation angle θ is used to locate the principal axes, which are just the symmetry axes for symmetric lesions. The angle θ is computed from $$\tan 2\theta = \frac{2\langle(x-x_c)(y-y_c)\rangle}{\langle(x-x_c)^2\rangle - \langle(y-y_c)^2\rangle}, \quad (7)$$

where the lesion intensity centroid is at $$x_c = \langle x \rangle \text{ and } y_c = \langle y \rangle. \quad (8)$$

The angular brackets in Eqs. (7) and (8) denote an intensity moment, which for any function f(x,y) of position in the image can be computed as follows:

$$\langle f(x, y)\rangle \equiv \frac{\sum_x \sum_y f(x, y) I_L(x, y)}{\sum_x \sum_y I_L(x, y)}, \quad (9)$$

where $I_L(x, y)$ is the segmented lesion image. In order to compare properties of different lesions, the parameters used are independent of the orientation of the lesion in the image. Therefore, the lesion asymmetry is determined with respect to the principal axes. The measure of asymmetry described here requires rotation of the image by an angle θ so that principal axes are parallel to the image axes. In this principal-axis coordinate system the following asymmetry factors are defined:

$$A_x = \frac{\sum_n \sum_y |I_L(x_c+n, y) - I_L(x_c-n, y)|}{\sum_x \sum_y I_L(x, y)}, \quad (10a)$$

$$A_y = \frac{\sum_x \sum_n |I_L(x, y_c+n) - I_L(x, y_c-n)|}{\sum_x \sum_y I_L(x, y)}. \quad (10b)$$

The asymmetry parameter, $$A = A_x + A_y, \quad (11)$$

is a measure of asymmetry in the geometric shape of a lesion as well as in the distribution of lesion pigmentation. Asymmetry parameters tend to be larger for malignant melanomas than for atypical melanocytic nevi.

Binary asymmetry parameter

If the intensity distribution $I_L$ in Eqs. (10a) and (10b) is replaced by the binary intensity distribution of Eq. (4), then the corresponding asymmetry parameter $A_{bin}$ is the fraction of the lesion pixels which do not have a counterpart on the other side of the principal axis. Thus, when based on the binary intensity distribution, parameter $A_{bin}$ is a measure of the asymmetry of the geometric shape of the lesion.

Lesion Blotchiness

Visually, many early malignant melanomas appear blotchy. In multispectral images there may be darker and lighter regions or blotches of rather homogeneous intensity. In color images, in contrast, there may be regions of different colors. Therefore, it is of interest to quantify such blotchiness in order to differentiate malignant from benign lesions.

Blotchiness Parameter Based on Spatial Intensity Distribution

The lesion is divided into $N_t$ "topographic" regions. If $I_{max}$ and $I_{min}$ are the maximum and minimum intensities in the lesion in some spectral band, respectively, then a pixel at (x,y) belongs to the nth region if $$I_{min} + (n-1)\frac{I_{max} - I_{min}}{N_t} \leq I_L(x, y) < I_{min} + n\frac{I_{max} - I_{min}}{N_t}. \quad (12)$$

For nth topographic region defined in Eq. (12), a distribution of distances of pixels in that region from the intensity centroid of the binary lesion mask $$d_n(x, y) = \sqrt{(x_n - x_c)^2 + (y_n - y_c)^2} \quad (13)$$

is obtained and its mean value $\langle d_n \rangle$ and variance $\text{Var}(d_n)$ are computed. The measure of lesion blotchiness based on spatial intensity distribution is $$Bl = \frac{\sum_{n=1}^{N_t} \sqrt{\text{Var}(d_n)}}{\sum_{n=1}^{N_t} \langle d_n \rangle}. \quad (14)$$

This parameter can be evaluated in every spectral band.

Blotchiness Parameter Baled on Centroids

The lesion is again divided into $N_t$ "topographic" regions as defined in Eq. (12). An intensity centroid $(x_c(n), y_c(n))$, defined in Eqs. (8) and (9), is then computed for each such region separately. The blotchiness parameter based on the centroid is defined as $$C = (X_{max} - X_{min})(Y_{max} - Y_{min})/A_l \quad (15)$$

where, for example, $X_{max}$ is the maximum value of $x_c(n)$, and $A_l$ is the lesion area in pixels. This blotchiness parameter is also determined in each spectral band separately.

Blotchiness Parameter Based on Spatial Color Distribution

The "color" in this analysis is not related to the visual perception of color. It is a quantitative descriptor of the relative intensities in red, blue, and green channels in a particular pixel.

All the other lesion parameters described here involve analysis of images in each spectral band separately. Therefore, absolute calibration of image intensities was not necessary. However, in order to describe the color distribution, normalization of intensities in red, green, and blue spectral bands is needed, so that intensities in the three channels are equal for white. In the spherical color coordinate system, $$R(x, y) = \frac{I_R(x, y)}{I_R(x, y) + I_B(x, y) + I_G(x, y)}, \quad (16)$$

$$G(x, y) = \frac{I_G(x, y)}{I_R(x, y) + I_B(x, y) + I_G(x, y)},$$

where the subscripts R, G, B refer to red, green, and blue spectral bands, are chosen as the independent variables. The lesion is then divided into color regions as follows. First $R(x,y)$ and $G(x,y)$ are divided into $N_R$ and $N_G$ topographic regions. A color region is defined as a particular combination of two topographic regions. The total number of color regions is $$N_C = N_R \times N_G. \quad (17)$$

The blotchiness parameter based on color is defined in analogy with Eq. (14):

$$Cl = \frac{\sum_{n=1}^{N_C} \sqrt{\text{Var}(d_n)}}{\sum_{n=1}^{N_C} \langle d_n \rangle}. \quad (18)$$

Lesion Border

Border Irregularity Parameter

Border irregularity is a well-known feature of malignant melanomas. It is typically defined as the ratio of the measured lesion perimeter to the perimeter of a circle with the same area as the lesion. Since perimeter is difficult to estimate reliably, a statistical descriptor of border irregularity is used here. In addition, many lesions are elongated and an ellipse is a better approximation for such lesions with regular borders than a circle.

Using the binary lesion mask of Eq. (4), the lesion intensity centroid from Eq. (8), orientation angle from Eq. (7), area, and the aspect ratio defined as $$AR = \frac{\sqrt{\langle x' - x_c \rangle^2}}{\sqrt{\langle y' - y_c \rangle^2}}, \quad (19)$$

where primes refer to the coordinate system defined by the lesion principal axes, are determined. These values are then used to construct an ellipse that is the best regular approximation to the lesion border. For each lesion border pixel at $(x_b, y_b)$, its angle with respect to the horizontal axis:

$$\phi = \tan^{-1}\frac{(x_b - x_c)}{(y_b - y_c)}, \quad (20)$$

and the location of the ellipse border for the same angle $(x_e(\phi), y_e(\phi))$ are determined. The distribution of distances between the ellipse border and lesion border:

$$d_{eb}(x_b, y_b) = d_b(x_b, y_b) - d_e(\phi), \quad (21)$$

where $$d_b(x_b, y_b) = \sqrt{(x_b - x_c)^2 + (y_b - y_c)^2} \quad (22)$$

and $$d_e(\phi) = \sqrt{x_e^2 + y_e^2}, \quad (23)$$

is obtained and the border irregularity parameter is defined as $$B = \frac{\sqrt{\mathrm{Var}(d_{eb})}}{\langle d_b \rangle}. \quad (24)$$

Border Gradient Parameter

Another parameter that quantitatively characterizes lesion border is the measure of intensity gradients across the lesion borders over the length scale defined by $n_g$, in units of pixels. For each lesion border pixel at $(x_b, y_b)$ one determines whether pixels at $(x_b \pm n_g, y_b \pm n_g)$ are at the border. If they are not, then the gradient is defined as $$G(x_b, y_b) = \tfrac{1}{2}[|I(x+n_g, y) - I(x-n_g, y)| + |I(x, y+n_g) - I(x, y-n_g)|]; \quad (25a)$$

otherwise, if pixels at $(x \pm n_g, y)$ are not on the border, $$G(x_b, y_b) = |I(x+n_g, y) - I(x-n_g, y)|, \quad (25b)$$

or, if pixels at $(x, y \pm n_g)$ are not on the border, $$G(x_b, y_b) = |I(x, y+n_g) - I(x, y-n_g)|. \quad (25c)$$

The border gradient parameter is defined as $$G = \frac{\sqrt{\mathrm{Var}(G)}}{\langle G \rangle}. \quad (26)$$

Lesion Texture

The description of lesion texture is particularly vulnerable to subjective judgement. The quantitative evaluation of lesion texture parameters is possible only using computer-based image analysis. While many such parameters are possible, those found to be helpful in discriminating between malignant melanomas and atypical melanocytic nevi are described below.

Texture Parameters Based on Local Intensity Variations

Texture parameters are defined over a length scale $n_t$ in units of pixels. For example, consider a pixel located at $(x,y)$ in the lesion. Let $I_l$ and $I_u$ be the minimum and the maximum intensities in an image in the $2n_t+1 \times 2n_t+1$ window around this pixel, i.e., in the range $[x-n_t, x+n_t]$ and $[y-n_t, y+n_t]$. Consider a variable $$C_1(x, y) = \frac{I_u - I_l}{I_l}. \quad (27)$$

The first two texture parameters are defined as:

$$T1 = \frac{\sqrt{\mathrm{Var}(C_1)}}{\langle C_1 \rangle} \quad (28)$$

and $$T2 = \sqrt{\mathrm{Var}(C_1)} \quad (29)$$

Another texture parameter uses the following variable:

$$C_3(x,y) = 4w(0,0) + w(-n_t,0) + w(n_t,0) + w(0,-n_t) + w(0,n_t) - 2[w(-n_t,-n_t) + w(-n_t,n_t) + w(n_t,-n_t) + w(n_t, n_t)] \quad (30)$$

where $$w(i,j) = I(x+i, y+j)/I(x,y). \quad (31)$$

If the value of $C_3$ is negative, it is set to zero and the corresponding texture parameter is $$T3 = \frac{\sqrt{\mathrm{Var}(C_3)}}{\langle C_3 \rangle}. \quad (32)$$

Another variable that leads to a texture parameter useful for classification of melanocytic lesions is:

$$C_4(x,y) = 8w(0,0) - w(-n_t,0) - w(n_t,0) - w(0,-n_t) - w(0,n_t) - w(-n_t,-n_t) - w(-n_t,n_t) - w(n_t,-n_t) - w(n_t,n_t) \quad (33)$$

Again, if the value of the variable is negative it is set to zero and the corresponding texture parameter is $$T4 = \frac{\sqrt{\mathrm{Var}(C_4)}}{\langle C_4 \rangle}. \quad (34)$$

Texture Parameters Based on Pigmented Network

Texture parameters have also been developed by considering the properties of a pigmented network. These texture parameters are measures of variability in the area of the dermal papillae and in the aspect ratio (length/width) of the rete ridges.

Since dermal papillae appear as the brighter part of the network, one seeks all the local maxima over a $2n_r+1 \times 2n_r+1$ window. Starting from such a maximum at $(x_m, y_m)$, one finds local one-dimensional minima in eight directions (2 vertical, 2 horizontal, and 4 diagonal) and locates the vertices of an octagonal region one pixel closer to the maximum intensity pixel than the minimum pixel. Such octagonal regions approximate the areas of dermal papillae $A_{dp}$ which are computed from the known location of vertices; the corresponding texture parameter is $$T5 = \frac{\sqrt{\mathrm{Var}(A_{dp})}}{\langle A_{dp} \rangle}. \quad (35)$$

Some of the areas determined by this algorithm are due to bubbles visible in some of these dermoscopic images. However, since there are typically on the order of hundreds of areas, and on the order of tens of bubbles, the statistical parameters should not be significantly biased by this artifact.

The aspect ratio of rete ridges is determined in a similar fashion, although one starts with local minima since rete ridges appear dark in the images. The vertices of an octagonal region are determined in this case from one-dimensional maxima in the eight directions. The maximum and minimum extents of this region are then determined and the aspect ratio R is computed. This texture parameter then is $$T6 = \frac{\sqrt{\text{Var}(R)}}{\langle R \rangle}. \tag{36}$$

III. LESION CLASSIFICATION

Selection of lesion parameters for classification was done by determining the maximum diagnostic accuracy for malignant melanoma for each parameter computed in every spectral band available for the training set of images. As mentioned above, diagnostic accuracy, sensitivity to malignant melanoma and specificity for the selected twenty two parameters are shown in FIG. 11. These parameters were then used as input to the linear classifier. Nonlinear classifiers may be used as well.

For each lesion k the linear classifier is $$L(k) = \sum_{n=1}^{22} w_n X_n(k), \tag{37}$$

where $X_n(k)$ are the parameters for the kth lesion and weights $w_n$ are to be determined so that a specified function $F(L)$ attains maximum value. The following functions $F(L)$ were used: 1) specificity under constraint of 100% sensitivity to malignant melanoma for the training set which included 41 malignant melanomas and 104 atypical melanocytic nevi; (2) classification accuracy for the 24 invasive and 16 noninvasive malignant melanomas of the training set; and 3) correlation with the Breslow thickness for the 24 invasive malignant melanomas.

Given any training set of lesion images and corresponding set of lesion image parameters, the weights that maximize $F(L)$ are found as follows. First, an initial range and resolution $\Delta$ for $w_n$ are selected. For each allowed set of values of $w_n$, the values $L(k)$ are computed for each lesion. The value $F(L)$ is determined based on the input from histopathological evaluation of the lesion based on a biopsy, such as the diagnosis of the lesion as benign or malignant, and the Breslow thickness for a malignant melanoma The range of $w_n$'s is adjusted until the maximum value of $F(L)$ is inside the range. Then the resolution $\Delta$ is reduced by a factor of two, and the process is repeated until $\Delta$ reaches specified minimum value $\Delta_{min}$. This procedure determines the weights $w_n$ only up to a multiplicative constant. It is noted that the classifiers resulting from a particular training set are applicable only to images with a specific spatial and spectral resolution, and that lesion images obtained with a different imaging system may require the development of different classifiers, by the procedures described above.

Figure 12:
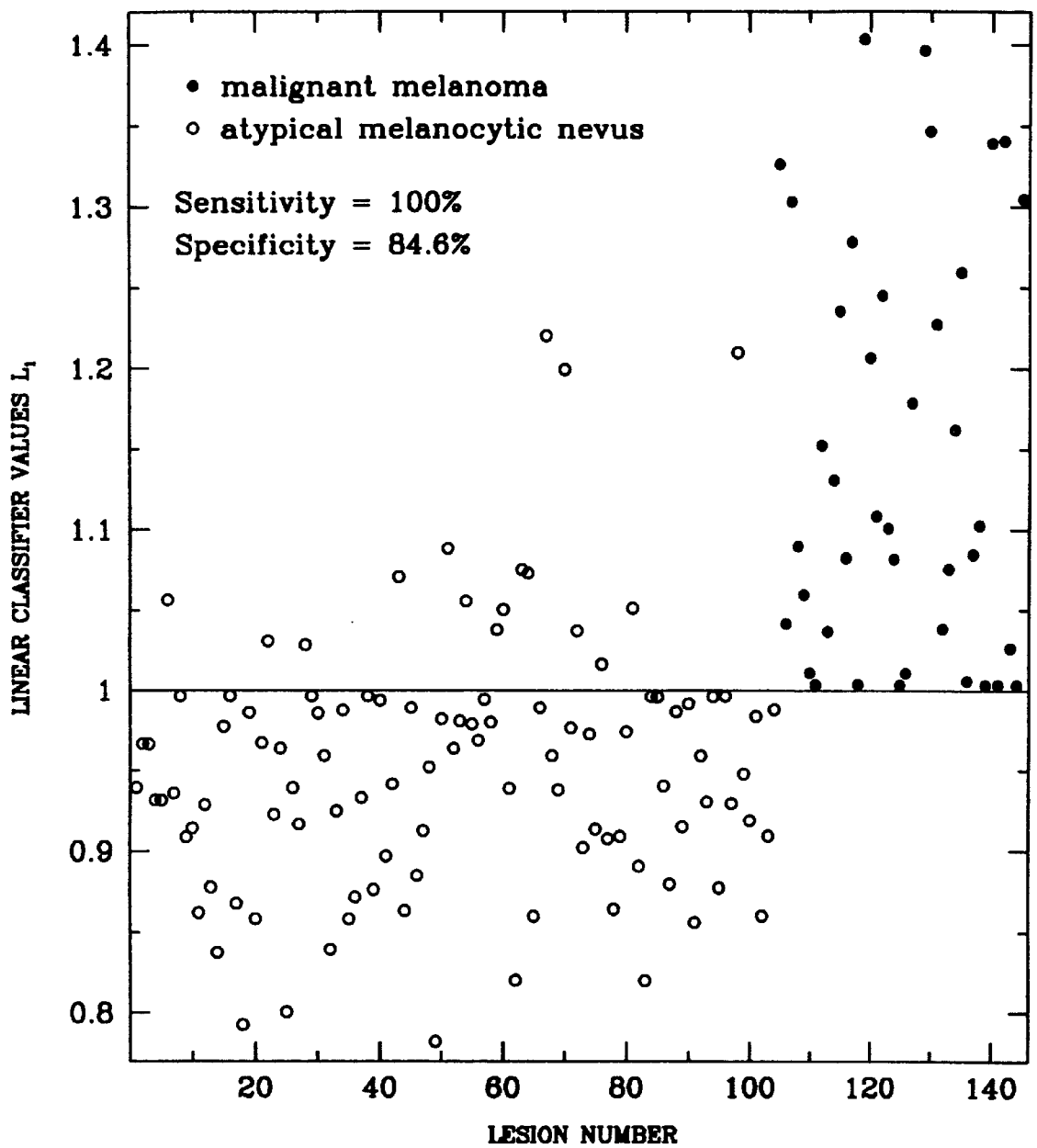
FIG. 12 is a plot of linear classifier values versus lesion identification number, for 41 malignant melanomas and 104 atypical melanocytic nevi.

Since detection of melanoma in its early stage significantly improves prognosis, there is a need for reliable methods of early detection. Clinical evaluation of melanocytic lesions is, however, a problem since reliable differentiation between early malignant melanoma with Breslow thickness less than 1 mm and atypical melanocytic nevus is difficult even for experienced dermatologists. In order to detect as many early melanomas as possible, weights in the linear classifier are preferably chosen to maximize specificity under the constraint of 100% sensitivity to malignant melanoma for the training set. For each set of weights, one finds the threshold value $L_{th}$ of the linear classifier such that a kth lesion is classified as suspicious of malignancy if $L(k) > L_{th}$, and as benign otherwise. The resulting classifier for the training set is $$L_1 = 0.025 A_{bin} + 0.090 A_b + 0.069 A_g + 0.160 A_r + 0.128 C_b + 0.095 Cl + 0.038 B + 0.107 T1_g + 0.064 T2_g + 0.018 T2_r + 0.111 T3_b + 0.167 T3_g + 0.268 T5_b \tag{38}$$

where the weights are normalized so that the threshold value equals one. This classifier with sensitivity to malignant melanoma of 100% and specificity of 85% is shown in FIG. 12. Statistical significance of the specificity and sensitivity was assessed by considering the binomial probabilities for the value of $L_1$ to exceed the threshold for the 41 malignant melanomas and 104 atypical melanocytic nevi of the training set separately. At the 95% confidence level, one finds that sensitivity is not less than 93% while specificity is not less than 79%. Since there are several melanomas very close to the threshold value, a practical classifier may use a threshold value that is less than one. It has been found that this set of 145 images is sufficient to yield statistically significant results. A greater number of images may be used, as well.

Figure 13:
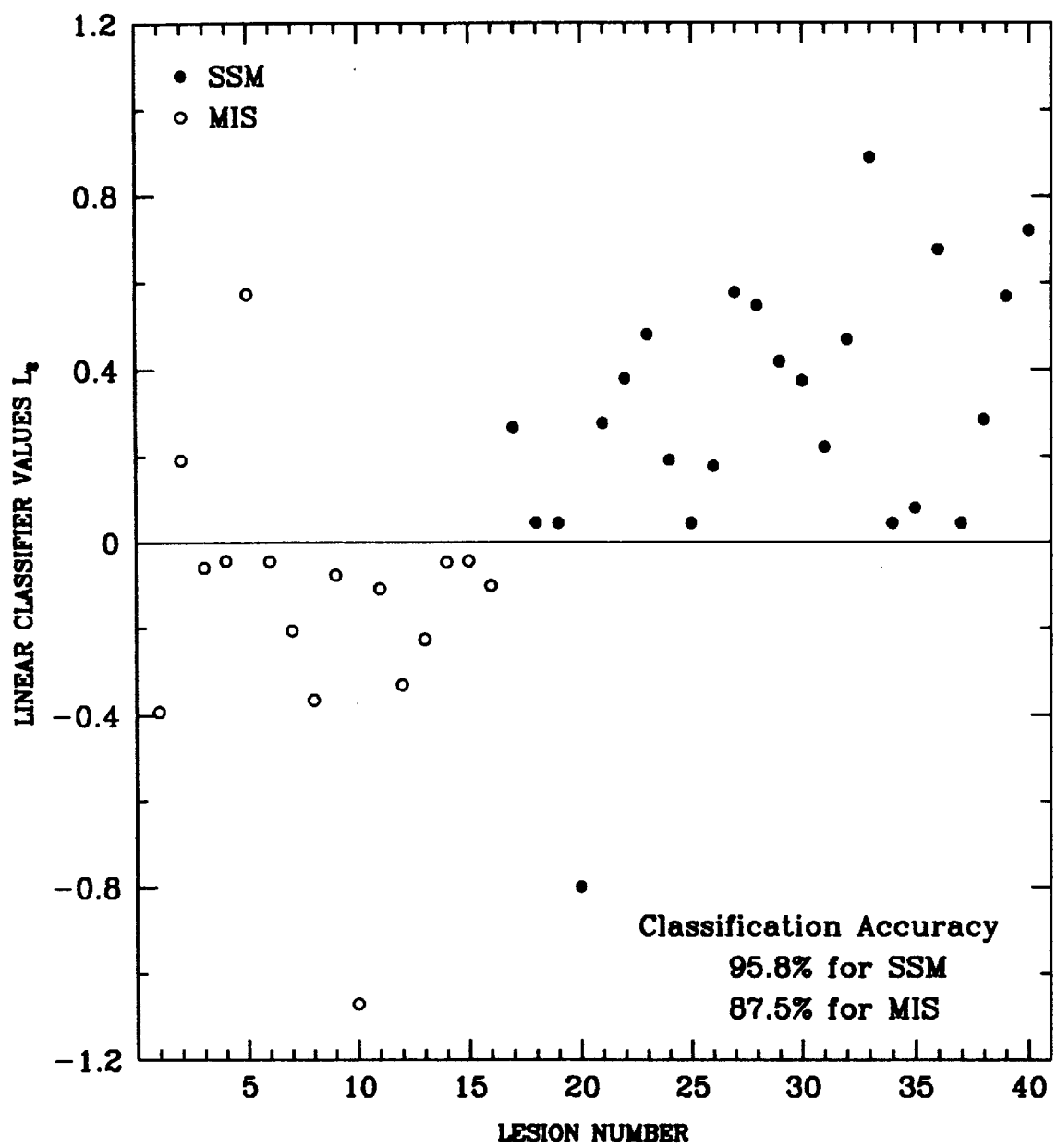
FIG. 13 is a plot of linear classifier values versus lesion identification number for 24 superficial spreading melanomas and 16 melanomas in-situ.

Some of the noninvasive melanomas, called melanomas in-situ, are confined to epidermis and are 100% curable by surgery. The invasive melanomas, i.e., superficial spreading melanomas in our data base, require more extensive surgery. Therefore, it is of clinical interest to differentiate between invasive and noninvasive melanomas and a linear classifier was trained to perform this task. This classifier, with weights chosen to maximize the over-all classification accuracy for the 24 superficial spreading melanomas and 16 melanomas in-situ of the training set is $$L_2 = -1.00 A_b - 0.14 Bl_g - 2.47 Bl_r - 0.4 C_b - 0.98 Cl - 1.17 T2_r + 0.53 T4_b + 1.98 T5_b + 1.58 T6_b - 0.73 \tag{39}$$

where a constant was subtracted from the classifier values to obtain the threshold value of zero. This classifier, with overall classification accuracy of 92.5%, is shown in FIG. 13.

Figure 14:
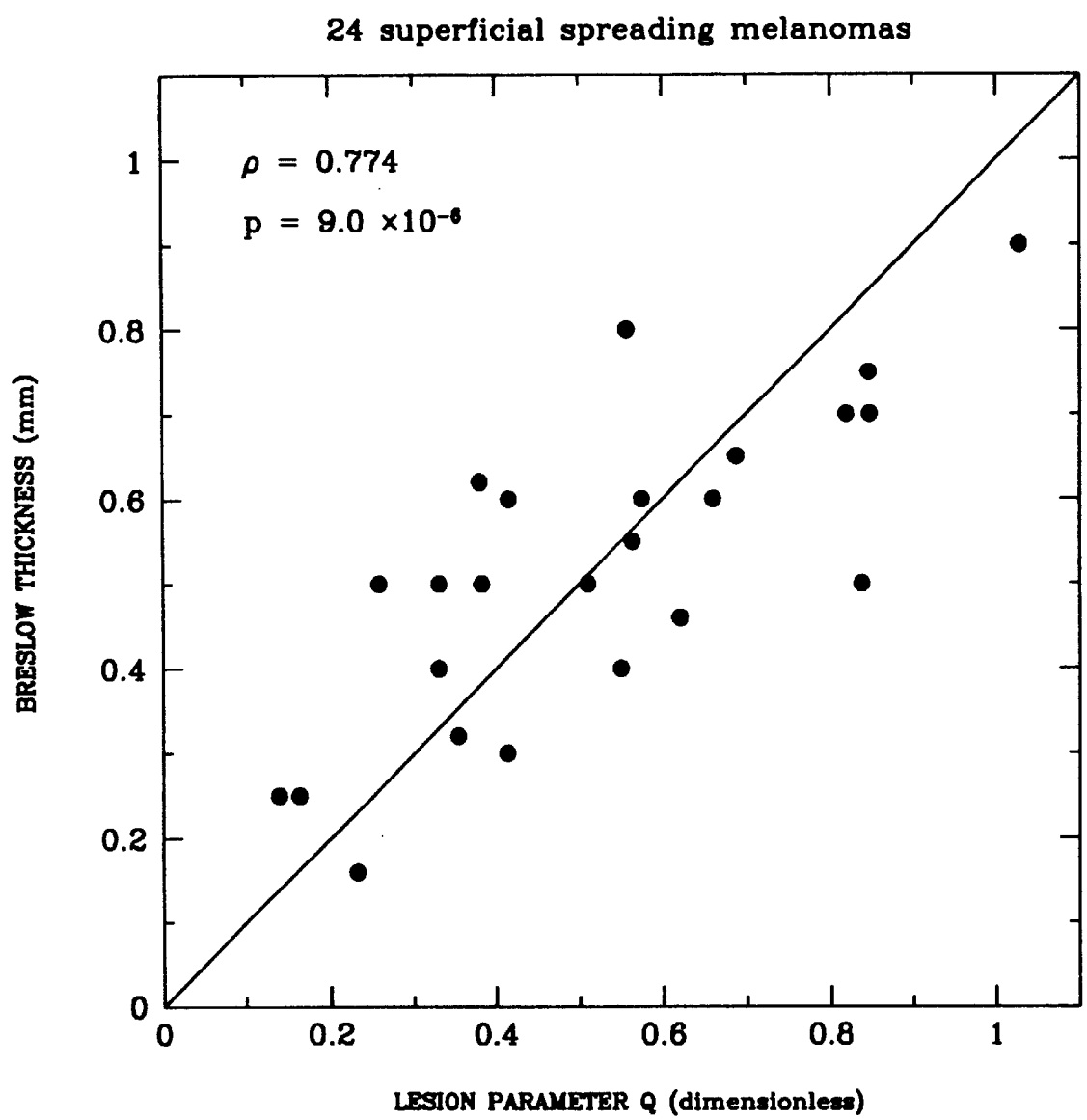
FIG. 14 is a plot of lesion parameter versus Breslow thickness for 24 superficial spreading melanomas.

Since prognosis for invasive melanomas correlates strongly with the Breslow thickness, a linear function of lesion parameters Q was trained to maximize the Pearson correlation co-efficient between Q and the Breslow thickness for a set 24 superficial spreading melanomas. This function is $$Q = 0.955 A_g - 1.391 A_r + 2.791 Bl_b - 1.320 Bl_g + 0.146 C_b + 0.267 C_r - 0.506 B + 0.202 T1_g + 1.476 T2_r - 0.485 \tag{40}$$

and is shown in FIG. 14. Even though there are only 24 superficial spreading melanomas in the data base, the high correlation of 0.77 is statistically very significant since $p = 9 \times 10^{-6}$.

The classifiers of Eqs. (38)–(40) are applicable to the imaging system described above, with respect to FIG. 1(a) wherein the monochrome camera 16 was used to digitize slides.

For other imaging systems, having different spatial and spectral resolution, different classifiers may need to be developed, based on a sufficient data base of lesion images obtained with that imaging system, in accordance with the procedures described above.

The segmentation, parameter estimation and classification programs described in Sections I–III, above, can be implemented on any personal computer, using a programming language, such as FORTRAN or C. The program can be stored on any convenient media readable by a computer, such as read only memory, ("ROM"), random access memory with a battery backup, electrically programmed ROM (EPROM), electrically erasable ROM (EEPROM), floppy disc, CD ROM, or a hard disc. Other suitable media may be used, as well.

While the procedures of Sections I–III were described with respect to digital images obtained by imaging color photographic slides of skin lesions with a monochrome CCD camera 16 in accordance with the system of FIG. 1c, these procedures are readily adaptable to the analysis of digital images of skin lesions acquired directly from the region of interest of the skin with a monochrome CCD camera 6 of FIG. 1a and FIG. 2.

In the process described in Sections I–III, above, segmentation was conducted in the blue wavelength band. The segmented mask in blue was then applied to images in the red and green wavelength bands. Where images at additional wavelengths are provided, segmentation is preferably first attempted at the shortest available spectral band where the contrast between the lesion and normal skin tends to be highest because of strong absorption by melanin. The segmented mask is then applied to the images in the remaining spectral bands. These steps are shown in FIG. 3b.

In addition, where parameters are described in terms of the red, green and blue wavelength bands in Section I–III, parameters can be derived at each of the other wavelengths used in the systems and methods above, in accordance with the procedures described in Section I–III. The additional parameters can be readily used to develop a classifier, also by the processes described in Section I–III.

The references cited above are incorporated by reference, herein.

While preferred systems and methods for practicing the present invention have been described above, it is understood that departures may be made from the systems and methods, without departing from the scope of the present invention, which is defined by the following claims.

We claim:

1. A method of characterizing a skin lesion wherein the absorption and scab of light in different spectral bands by the skin lesion is a function of the condition of the skin, the method comprising:

illuminating a portion of the skin including the region of interest by light in at least three spectral bands;

digitally imaging a portion of the skin including the region of interest at the at least three spectral bands with the light re-emitted by the portion of the skin to generate digital images comprising digital signals whose values are a function of the condition of the region of interest of the skin; and providing the digital images to a processor, wherein the processor:

segments the digital image by generating a single segmentation mask defining the boundary of the region of interest for each image, where the single segmentation mask is the segmentation mask having largest area of segmentation masks generated from each image in each of the at least three spectral bands, without operator intervention;

automatically computes at least one estimated value for each digital image at each spectral band which is a function of a characteristic of the portion of the region of interest determined by the segmentation mask, without operator intervention;

characterizes the condition of the skin as malignant or benign based on the estimated values, without operator intervention; and outputs the characterization of the condition of the skin.

2. The method of claim 1, further comprising estimating at least one value which is a function of the texture of the region of interest.

3. The method of claim 2, wherein the computing step comprises estimating values which are statistical measures of local intensity variation in the digital images in each spectral band, which are a function of the texture of the region of interest.

4. The method of claim 2, wherein the computing step comprises estimating values based on the ratio of standard deviation of the areas of dermal papillae to their mean within the segmentation mask.

5. The method of claim 2, wherein the computing step comprises estimating values of the average and standard deviation of the thickness of rete ridges within the segmentation masks.

6. The method of claim 1, further comprising estimating at least one value which is a function of the asymmetry of the region of interest in each spectral band, for two principal axes of the segmented image by:

determining the principal axes of the segmented image;

rotating the principal axes of the segmented image until they are oriented parallel to the coordinate axes of the image;

computing the differences in intensity between each pair of pixels whose locations, with respect to a principal axis, are mirror images of each other;

summing the absolute values of said intensity differences;

calculating asymmetry values with respect to each principal axis, by normalizing the said sum to the total intensity in the segmented images; and adding together the asymmetry values calculated for the two principal axes.

7. The method of claim 1, further comprising estimating at least one value which is a function of the blotchiness of the region of interest.

8. The method of claim 1, further comprising estimating at least one value which is a function of the irregularity of the border of the region of interest by estimating a value which is a statistical measure of the deviation of the border of the segmentation mask from the border of an ellipse of the same area, aspect ratio, and orientation as the segmentation mask.

9. The method of claim 1, further comprising estimating a value which is a function of the gradient at the border of the region of interest by estimating a statistical measure of the gradient values of the intensity of the digital images across the border of the segmented images, at each spectral band.

10. The method of claim 1, further comprising characterizing the type of lesion as invasive or non-invasive.

11. The method of claim 1, wherein the segmenting step comprises generating the segmentation mask from a digital image by:

removing digital signals from the digital image which correspond to hair structures;

deriving a threshold from a multimodal histogram of intensity levels;

iteratively applying the threshold to the digital signals of the digital image; and removing digital signals which correspond to small blob-like regions from the masked image.

12. The method of claim 1, wherein the digital imaging step further comprises digitally imaging the region of interest with a digital camera.

13. The method of claim 1, further comprising:

photographing the region of interest with a color camera to form color photographic slides; and illuminating the color photographic slides with light in each spectral band;

wherein the digital imaging step comprises digitally imaging the illuminated color photographic slides of the region of interest with a digital camera.

14. The method of claim 1, where the characterization step is based on a non-linear combination of the estimated values.

15. The method of claim 1, where the characterization step is based on a linear combination of the estimated values.

16. The method of claim 1, where the characterization step is based on a sequential combination of applying a linear combination of the estimated values and a non-linear combination of estimated values.

17. A method of characterizing the condition of a region of interest of skin, wherein the absorption and scattering of light in different spectral bands by the region of interest is a function of the condition of the skin, the method comprising:

illuminating a portion of the skin including the region of interest by light in at least thee spectral bands;

digitally imaging the portion of the skin including the region of interest at the at least tree spectral bands with the light re-emitted by the portion of the skin to generate digital images comprising digital signals whose values are a function of the condition of the region of interest of the skin; and providing the digital images to a processor, wherein the processor:

segments the digital images by generating a single segmentation mask defining the boundary of the region of interest for each image, where the single segmentation mask is the segmentation mask having largest area of segmentation masks generated from each image in each of the at least three spectral bands;

computes at least one estimated value for each digital image at each spectral band which is a function of a characteristic of the region of interest determined by the segmentation mask;

characterizes the condition of the region of interest of the skin based on the estimated values; and outputs the characterization of the condition of the region of interest of the skin.

18. The method of claim 17, wherein the estimating and characterizing steps are conducted without the intervention of an operator.

19. The method of claim 17, wherein the segmenting step is conducted without the intervention of an operator.

20. The method of claim 17, wherein the illuminating step further comprises illuminating the region of interest with light in at least one spectral band which penetrates to the papillary dermis and is re-emitted therefrom.

21. The method of claim 20, wherein the digital imaging step further comprises digitally imaging the region of interest with a digital camera.

22. The method of claim 20, wherein the illuminating step further comprises illuminating the region of interest with light in a near infrared spectral band.

23. The method of claim 17, further comprising suppressing specular reflections prior to the digital imaging step.

24. The method of claim 23, wherein the processor converts the digital signals of each of the digital images into values corrected for non-uniformities of illumination and of response prior to the segmenting step.

25. The method of claim 17, further comprising:

photographing the region of interest with a color camera to form color photographic slides; and illuminating the color photographic slides with light in each spectral band;

wherein the digital imaging step comprises digitally imaging the illuminated color photographic slides of the region of interest with a digital camera.

26. The method of claim 17, wherein the segmenting step further comprises applying the segmentation mask to the digital images in the other spectral bands.

27. The method of claim 17, wherein the segmenting step comprises generating the mask at the shortest available wavelength.

28. The method of claim 17, wherein the illuminating step comprises illuminating the region of interest by light in at least one spectral band whose center is between about 400 to about 500 nanometers, and the segmenting step comprises generating the mask from a digital image at the spectral band between about 400 to about 500 nanometers.

29. The method of claim 19, wherein the segmenting step comprises generating the segmentation mask from a digital image by:

removing digital signals from the digital image which correspond to hair structures;

deriving a threshold from a multimodal histogram of intensity levels;

iteratively applying the threshold to the digital signals of the digital image; and removing digital signals which correspond to small blob-like regions from the masked image.

30. The method of claim 19, wherein the segmenting step comprises generating the segmentation mask by comparing estimated values which are a function of textures within the digital images with a threshold.

31. The method of claim 30, further comprising generating the segmentation mask by comparing the estimated texture values to a threshold derived through statistical analysis of each digital image.

32. The method of claim 17, wherein the computing step comprises estimating at least one value which is a function of the texture of the region of interest determined by the segmentation mask.

33. The method of claim 32, wherein the computing step further comprises estimating values which are a function of the texture of the region of interest determined by the segmentation mask separately in each spectral band, based on the same segmentation mask.

34. The method of claim 32, wherein the computing step comprises estimating values which are statistical measures of local intensity variation in the digital images in each spectral band which are a function of texture.

35. The method of claim 17, wherein the computing step further comprises estimating a value which is a function of the asymmetry of the segmented image in each spectral band, for two principal axes of the segmented image.

36. The method of claim 35, wherein the computing step further comprises:

locating the principal axes by computing an orientation angle;

computing the intensity centroid;

rotating the digital image such that the principal axes are parallel to the image axes;

estimating asymmetry values for each principal axis based on the intensity centroid; and summing the estimated asymmetry values for the two principal axes.

37. The method of claim 36, wherein the computing step further comprises computing the intensity moment with a binary intensity distribution.

38. The method of claim 17, wherein the computing step further comprises estimating at least one value which is a function of the blotchiness of the segmented digital image, the estimated blotchiness value being defined through statistical properties of the spatial distribution of topographic regions of the digital images at each spectral band.

39. The method of claim 38, wherein the computing step further comprises determining the centroids of topographic regions of the segmented digital image at each spectral band.

40. The method of claim 17, wherein the characterizing step comprises comparing a weighted combination of estimated values against a threshold value.

41. The method of claim 40, wherein the condition of the region of interest to be characterized is the presence of a melanoma and weight coefficients for each estimated value and the threshold value are selected to maximize specificity, under the constraint of a defined sensitivity to melanoma, on a representative set of training images.

42. The method of claim 17, where the characterization step is based on a non-linear combination of the estimated values.

43. The method of claim 17, where the characterization step is based on a linear combination of the estimated values.

44. The method of claim 17, where the characterization step is based on a sequential combination of applying a linear combination of the estimated values and a non-linear combination of estimated values.

45. A system for characterizing the condition of a region of interest of skin, comprising:
a source of illumination of light in at least three spectral bands;
a camera for acquiring digital images of the region of interest based on the light re-emitted from the illuminated region of interest at each of the spectral bands, the digital image comprising digital signals whose values are a function of the condition of the region of interest;
memory for storing the digital images provided by the camera;
a digital processor programmed to perform the steps of:
segmenting the digital images stored in memory by generating a single segmentation mask, where the single segmentation mask is the segmentation mask having largest area of segmentation masks generated from each image in each of the at least three spectral bands;
estimating at least one value for each digital image at each spectral band which is a function of the texture of the portion of the region of interest determined by the segmentation mask;
characterizing the condition of the skin based on the estimated values; and
outputting the characterization of the region of interest.

46. The system of claim 45, further comprising means for suppressing specular reflections from the region of interest.

47. The system of claim 45, further comprising means for calibrating each digital image to provide correction for non-uniformities of illumination and response.

48. The system of claim 45, wherein the digital processor is coupled to the source of illumination and to the camera for controlling the intensity of illumination and exposure times, respectively.

49. The system of claim 45, wherein the processor applies the segmentation mask derived from the digital images at one spectral band to the digital images at the other spectral bands.

50. The system of the claim 45, where in the processor estimates values separately from digital images at each spectral band based on the segmentation mask.

51. The system of claim 49, wherein the processor compares a weighted combination of estimated values against a threshold value.

52. The system of claim 45, wherein the camera records monochromatic images and the illumination means comprises:
a tungsten halogen light source with feedback to stabilize the intensity in each wavelength band;
means for sequentially filtering the light; and
an optical fiber ring illuminator to distribute the filtered light.

53. The system of claim 45, further comprising a feedback loop for stabilizing the intensity of the light source by the processor.

54. The system of claim 45, wherein the filter means comprises a plurality of interference filters mounted on a wheel for stepping any filter into a position intercepting the light from the light source.

55. The system of claim 45, wherein at least one of the spectral bands has a center which is between about 400 to about 500 nanometers, and at least one other band centered elsewhere in the visible region.

56. The system of claim 55, wherein the set of interference filters includes a filter whose center lies in at least one spectral band in the near infrared range whose center lies between about 750 and 1000 nanometers.

57. The system of claim 50, wherein the camera is a single-chip, charge-coupled device and the control means comprises a digital computer including means for determining exposure times for the camera which maximize the signal-to-noise ratio in the image at each spectral band.

58. The system of claim 45, wherein:
the source of illumination provides broad-band ("white") light; and
the camera comprises multiple charge-coupled devices which detect light in a plurality of spectral bands between the near ultraviolet to near infrared.

59. The system of claim 45, wherein the processor estimates values which are statistical measures of local intensity variation in the digital images in each spectral band, which are a function of the texture of the region of interest.

60. The system of claim 45, wherein the processor estimates values based on the ratio of standard deviation of the areas of dermal papillae to their mean within the segmentation mask.

61. The system of claim 45, wherein the processor estimates values of the average and standard deviation of the thickness of rete ridges within the segmentation masks.

62. The system of claim 45, wherein the processor estimates at least one value which is a function of the asymmetry of the region of interest in each spectral band, for two principal axes of the segmented image by:
locating the principal axes by computing an orientation angle;
computing the intensity centroid;
rotating the digital image such that the principal axes are parallel to the image axes; and
estimating asymmetry values for each principal axis based on the intensity centroid; and
summing the estimated asymmetry values for the two principal axes.

63. The system of claim 45, wherein the processor further estimates at least one value which is a function of the blotchiness of the region of interest.

64. The system of claim 45, wherein the processor further estimates at least one value which is a function of the irregularity of the border of the region of interest by estimating a value which is a statistical measure of the deviation of the border of the segmentation mask from the border of an ellipse of the same area, aspect ratio, and orientation as the segmentation mask.

65. The system of claim 45, wherein the processor further estimates a value which is a function of the gradient at the border of the region of interest by estimating a statistical measure of the gradient values of the intensity of the digital images across the border of the segmented images, at each spectral band.

66. The system of claim 45, wherein the processor characterizes the type of lesion as invasive or non-invasive.

67. The system of claim 45, wherein the processor generates the segmentation mask from a digital image by:
   removing digital signals from the digital image which correspond to hair structures;
   deriving a threshold from a multimodal histogram of intensity levels;
   iteratively applying the threshold to the digital signals of the digital image; and
   removing digital signals which correspond to small blob-like regions from the masked image.

68. A system for characterizing the condition of a region of interest of skin, comprising:
   a source of illumination of light in at least three spectral bands;
   a camera for acquiring digital images of the region of interest based on the light re-emitted from the illuminated region of interest at each of the at least three spectral bands, the digital image comprising digital signals whose values are a function of the condition of the region of interest;
   a memory for storing the digital images;
   a digital processor including:
      digital processing means for segmenting the digital images stored in memory and computing estimated values of parameters which are a function of the segmented images, wherein the digital images are segmented by generating a single segmentation mask, where the single segmentation mask is the segmentation mask having largest area of segmentation masks generated from each image in each of the at least three spectral bands;
      digital processing means for automatically characterizing the condition of the tissue based on the estimated values; and
      means for outputting the characterization of the region of interest.

69. A method of characterizing the condition of a region of interest of skin, wherein the absorption and scattering of light in different spectral bands by the region of interest is a function of the condition of the skin, the method comprising:
   illuminating a portion of the skin including the region of interest by light in at least three spectral bands;
   digitally imaging the portion of the skin including the region of interest at the at least three spectral bands with the light re-emitted by the portion of the skin to generate digital images comprising digital signals whose values are a function of the condition of the region of interest of the skin; and
   providing the digital images to a processor, wherein the processor:
      segments the digital images by generating a segmentation mask defining the boundary of the region of interest from a digital image in any one of the at least three spectral bands;
      computes at least one estimated value which is a statistical measure of the deviation of the boundary of the region of interest from the boundary of an ellipse of the same area, aspect ratio, and orientation as the segmentation mask;
      characterizes the condition of the region of interest of the skin based on the estimated values; and
      outputs the characterization of the condition of the region of interest of the skin.

70. A method of characterizing the condition of a region of interest of skin, wherein the absorption and scattering of light in different spectral bands by the region of interest is a function of the condition of the skin, the method comprising:
   illuminating a portion of the skin including the region of interest by light in at least three spectral bands;
   digitally imaging the portion of the skin including the region of interest at the at least three spectral bands with the light re-emitted by the portion of the skin to generate digital images comprising digital signals whose values are a function of the condition of the region of interest of the skin; and
   providing the digital images to a processor, wherein the processor:
      segments the digital images by generating a segmentation mask defining the boundary of the region of interest from a digital image in any one of the at least three spectral bands;
      computes at least one estimated value of a statistical measure of the gradient values of the intensity of the digital images across the border of the segmented images;
      characterizes the condition of the region of interest of the skin based on the estimated values; and
      outputs the characterization of the condition of the region of interest of the skin.

71. A method of characterizing the condition of a region of interest of skin, wherein the absorption and scattering of light in different spectral bands by the region of interest is a function of the condition of the skin, the method comprising:
   illuminating a portion of the skin including the region of interest by light in at least three spectral bands;
   digitally imaging the portion of the skin including the region of interest at the at least three spectral bands with the light re-emitted by the portion of the skin to generate digital images comprising digital signals whose values are a function of the condition of the region of interest of the skin; and
   providing the digital images to a processor, wherein the processor:
      segments the digital images by generating a segmentation mask defining the boundary of the region of interest from a digital image in any one of the at least three spectral bands;
      computes at least one estimated value based on the ratio of standard deviation of the areas of dermal papillae to their mean within the segmentation mask;
      characterizes the condition of the region of interest of the skin based on the estimated values; and
      outputs the characterization of the condition of the region of interest of the skin.

72. A method of characterizing the condition of a region of interest of skin, wherein the absorption and scattering of light in different spectral bands by the region of interest is a function of the condition of the skin, the method comprising:
   illuminating a portion of the skin including the region of interest by light in at least three spectral bands;

digitally imaging the portion of the skin including the region of interest at the at least three spectral bands with the light re-emitted by the portion of the skin to generate digital images comprising digital signals whose values are a function of the condition of the region of interest of the skin; and providing the digital images to a processor, wherein the processor:

segments the digital images by generating a segmentation mask defining the boundary of the region of interest from a digital image in any one of the at least three spectral bands;

computes at least one estimated value of the average and standard deviation of the thickness of rete ridges within the segmentation mask for a digital image of the region of interest determined by the segmentation mask;

characterizes the condition of the region of interest of the skin based on the estimated values; and outputs the characterization of the condition of the region of interest of the skin for a digital image of the region of interest determined by the segmentation mask.

73. A method of characterizing the condition of a region of interest of skin, wherein the absorption and scattering of light in different spectral bands by the region of interest is a function of the condition of the skin, the method comprising:

illuminating a portion of the skin including the region of interest by light in at least three spectral bands;

digitally imaging the portion of the skin including the region of interest at the at least three spectral bands with the light re-emitted by the portion of the skin to generate digital images comprising digital signals whose values are a function of the condition of the region of interest of the skin;

calibrating each pixel location in the digital image in each spectral band with respect to stored images of a white target material having known diffuse reflectance, each of the stored images being an average of a plurality of images acquired at each spectral band, while the material undergoes continual in-plane motion; and providing the digital images to a processor, wherein the processor:

segments the digital images by generating a segmentation mask defining the boundary of the region of interest from a digital image in any one of the at least three spectral bands;

computes at least one estimated value for each digital image at each spectral band which is a function of a characteristic of the region of interest determined by the segmentation mask;

characterizes the condition of the region of interest of the skin based on the estimated values; and outputs the characterization of the condition of the region of interest of the skin.

* * * * *

UNITED STATES PATENT AND TRADEMARK OFFICE
CERTIFICATE OF CORRECTION

| | | |
|---|---|---|
| PATENT NO. | : 6,208,749 B1 | Page 1 of 1 |
| APPLICATION NO. | : 09/032450 | |
| DATED | : March 27, 2012 | |
| INVENTOR(S) | : Gutkowicz-Krusin et al. | |

It is certified that error appears in the above-identified patent and that said Letters Patent is hereby corrected as shown below:

In Claim 17, column 25, line 22, please delete "tree" and insert --three--.

Signed and Sealed this
Fourteenth Day of August, 2012

David J. Kappos
*Director of the United States Patent and Trademark Office*